US010737944B2

(12) United States Patent
Vautravers et al.

(10) Patent No.: US 10,737,944 B2
(45) Date of Patent: Aug. 11, 2020

(54) TIN-CONTAINING ZEOLITIC MATERIAL HAVING A BEA FRAMEWORK STRUCTURE

(71) Applicant: BASF SE, Ludwigshafen am Rhein (DE)

(72) Inventors: Nicolas Vautravers, Mannheim (DE); Joaquim Henrique Teles, Waldsee (DE); Ralf Pelzer, Fürstenberg (DE); Daniel Schneider, Frankenthal (DE); Florian Garlichs, Neustadt (DE); Andreas Keller, Speyer (DE); Andrei-Nicolae Parvulescu, Ruppertsberg (DE); Ulrich Müller, Neustadt (DE); Sumana Roy, Frankfurt (DE)

(73) Assignee: BASF SE (DE)

( * ) Notice: Subject to any disclaimer, the term of this patent is extended or adjusted under 35 U.S.C. 154(b) by 244 days.

(21) Appl. No.: 16/060,260

(22) PCT Filed: Dec. 7, 2016

(86) PCT No.: PCT/EP2016/080015
§ 371 (c)(1),
(2) Date: Jun. 7, 2018

(87) PCT Pub. No.: WO2017/097806
PCT Pub. Date: Jun. 15, 2017

(65) Prior Publication Data
US 2018/0362353 A1 Dec. 20, 2018

(30) Foreign Application Priority Data
Dec. 8, 2015 (EP) .................... 15198365

(51) Int. Cl.
C01B 39/12 (2006.01)
B01J 29/86 (2006.01)
C01B 39/02 (2006.01)
C07C 45/54 (2006.01)
C07C 67/39 (2006.01)
C01B 39/06 (2006.01)
B01J 29/70 (2006.01)
B01J 37/02 (2006.01)
B01J 35/10 (2006.01)

(52) U.S. Cl.
CPC ........... C01B 39/12 (2013.01); B01J 29/7057 (2013.01); B01J 29/86 (2013.01); B01J 35/1019 (2013.01); B01J 37/0207 (2013.01); C01B 39/026 (2013.01); C01B 39/06 (2013.01); C07C 45/54 (2013.01); C07C 67/39 (2013.01); B01J 2229/183 (2013.01); B01J 2229/34 (2013.01); B01J 2229/37 (2013.01); C01P 2002/70 (2013.01); C01P 2002/82 (2013.01); C01P 2002/84 (2013.01); C01P 2006/12 (2013.01)

(58) Field of Classification Search
CPC ....... C01B 39/026; C01B 39/06; C01B 39/12; C01P 2002/84; C01P 2006/12; B01J 29/7057; B01J 29/86; B01J 35/1019; B01J 37/0207; B01J 2229/24; B01J 2229/37; B01J 2229/183
See application file for complete search history.

(56) References Cited

U.S. PATENT DOCUMENTS

| 9,108,190 B1* | 8/2015 | Fan .................... B01J 29/89 |
| 9,446,390 B2 | 9/2016 | Parvulescu et al. |
| 9,540,305 B2 | 1/2017 | Parvulescu et al. |
| 9,695,099 B2 | 7/2017 | Liu et al. |
| 9,765,001 B2 | 9/2017 | Rudenauer et al. |
| 9,765,003 B2 | 9/2017 | Vautravers et al. |
| 9,796,654 B2 | 10/2017 | Vautravers et al. |
| 9,856,199 B2 | 1/2018 | Hickmann et al. |
| 9,920,007 B2 | 3/2018 | Rudenauer et al. |
| 9,950,982 B2 | 4/2018 | Bru Roig et al. |
| 9,969,708 B2 | 5/2018 | Vautravers et al. |
| 9,975,837 B2 | 5/2018 | Schelwies et al. |
| 9,988,268 B2 | 6/2018 | Riedel et al. |
| 9,999,878 B2* | 6/2018 | Parvulescu .......... B01J 29/7007 |
| 10,414,664 B2* | 9/2019 | Gounder ............. B01J 29/7007 |
| 2016/0312149 A1 | 10/2016 | Vautravers et al. |
| 2016/0318860 A1 | 11/2016 | Vautravers et al. |
| 2016/0325228 A1 | 11/2016 | Feyen et al. |
| 2017/0037021 A1 | 2/2017 | Stork et al. |
| 2017/0037296 A1 | 2/2017 | Kimura et al. |
| 2017/0044421 A1 | 2/2017 | Parvulescu et al. |
| 2017/0128916 A1 | 5/2017 | Lejkowski et al. |
| 2017/0173570 A1* | 6/2017 | Holm .................. B01J 29/7049 |

(Continued)

FOREIGN PATENT DOCUMENTS

CN 104709920 A 6/2015
WO WO-0181291 A2 11/2001
(Continued)

OTHER PUBLICATIONS

Dijkmans, J., et al., "Post-synthesis Snβ: An exploration of synthesis parameters and catalysis", Journal of Catalysis, vol. 330, (2015), pp. 545-557.
Hammond, C., et al., "Simple and Scalable Preparation of Highly Active Lewis Acidic Sn-β", Angewandte Chemie International Edition, vol. 51, No. 47, (2012), pp. 11736-11739.
International Search Report for PCT/EP2016/080015 dated Jan. 24, 2017.
International Search Report for PCT/EP2016/080076 dated Jan. 24, 2017.
Kang, Z., et al., "Preparation and Characterization of Sn-β Zeolites by a Two-Step Postsynthesis Method and Their Catalytic Performance for Baeyer-Villiger Oxidation of Cyclohexanone", Chinese Journal of Catalysis, vol. 33, No. 5, (2012), pp. 898-904.
(Continued)

Primary Examiner — David M Brunsman
(74) Attorney, Agent, or Firm — Faegre Drinker Biddle & Reath LLP

(57) ABSTRACT

An incipient wetness impregnation method for preparing a tin-containing zeolitic material having framework type BEA, a novel tin-containing zeolitic material having framework type BEA and its use.

20 Claims, 14 Drawing Sheets

(56) References Cited

U.S. PATENT DOCUMENTS

Figure 1:
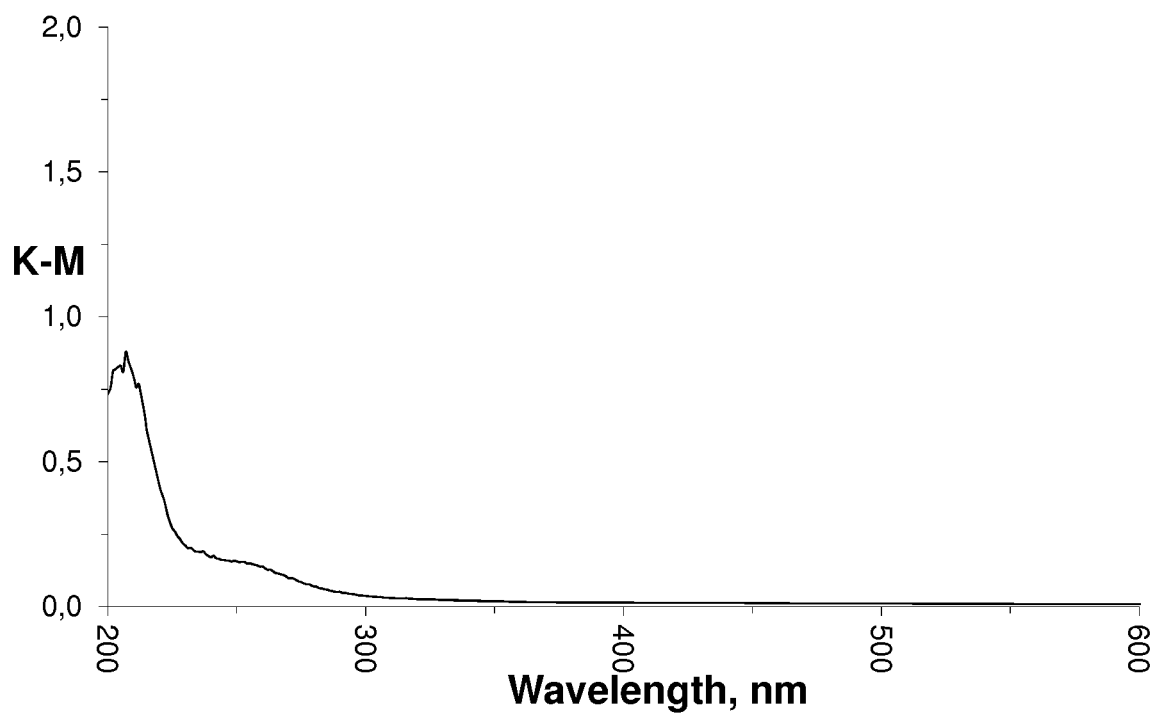

| | | |
|---|---|---|
| 2017/0225959 A1 | 8/2017 | Maurer et al. |
| 2017/0233780 A1 | 8/2017 | Breuer et al. |
| 2017/0233874 A1 | 8/2017 | Aust et al. |
| 2017/0246620 A1 | 8/2017 | Parvulescu et al. |
| 2017/0275076 A1 | 9/2017 | Edgington et al. |
| 2017/0275225 A1 | 9/2017 | Riedel et al. |
| 2017/0283352 A1 | 10/2017 | Fenlon et al. |
| 2017/0292084 A1 | 10/2017 | Stork et al. |
| 2017/0334820 A1 | 11/2017 | Pelzer et al. |
| 2017/0334824 A1 | 11/2017 | Pelzer et al. |
| 2017/0336030 A1 | 11/2017 | Weickert et al. |
| 2017/0362532 A1 | 12/2017 | Pelzer et al. |
| 2018/0022611 A1 | 1/2018 | Feyen et al. |
| 2018/0036723 A1 | 2/2018 | Riedel et al. |
| 2018/0044313 A1 | 2/2018 | Rudenauer et al. |
| 2018/0105838 A1 | 4/2018 | Schrader et al. |
| 2018/0133700 A1* | 5/2018 | Brunelli ............... B01J 29/7007 |
| 2018/0134570 A1 | 5/2018 | Maurer et al. |
| 2018/0134680 A1 | 5/2018 | Siegel et al. |
| 2018/0170850 A1 | 6/2018 | Vautravers et al. |
| 2018/0171262 A1 | 6/2018 | Rudenauer et al. |
| 2018/0334389 A1* | 11/2018 | Mintova Lazarova .. B01J 29/89 |

FOREIGN PATENT DOCUMENTS

| | | | | |
|---|---|---|---|---|
| WO | WO-2013117537 A1 * | 8/2013 | ............. | C01B 39/12 |
| WO | WO-2015067654 A1 | 5/2015 | | |
| WO | WO-2015123530 A1 | 8/2015 | | |
| WO | WO-2015123531 A1 | 8/2015 | | |
| WO | WO-2015197699 A1 | 12/2015 | | |
| WO | WO-2016024201 A1 | 2/2016 | | |
| WO | WO-2016074918 A1 | 5/2016 | | |
| WO | WO-2016075100 A1 | 5/2016 | | |
| WO | WO-2016075129 A1 | 5/2016 | | |
| WO | WO-2016135133 A1 | 9/2016 | | |
| WO | WO-2016180809 A1 | 11/2016 | | |
| WO | WO-201760440 A1 | 4/2017 | | |
| WO | WO-2017067841 A1 | 4/2017 | | |
| WO | WO-2017067843 A1 | 4/2017 | | |
| WO | WO-2017085049 A1 | 5/2017 | | |
| WO | WO-2017089327 A1 | 6/2017 | | |
| WO | WO-2017089344 A1 | 6/2017 | | |
| WO | WO-2017089410 A1 | 6/2017 | | |

OTHER PUBLICATIONS

Liu, M., et al., "Facile preparation of Sn-β zeolites by post-synthesis (isomorphous substitution) method for isomerization of glucose to fructose", Chinese Journal of Catalysis, vol. 35, No. 5, (2014), pp. 723-732.
Written Opinion of the International Searching Authority for PCT/EP2016/080015 dated Jan. 24, 2017.
Written Opinion of the International Searching Authority for PCT/EP2016/080076 dated Jan. 24, 2017.
U.S. Appl. No. 61/939,889.
U.S. Appl. No. 61/939,895.
U.S. Appl. No. 61/939,896.
U.S. Appl. No. 61/990,490.
U.S. Appl. No. 61/990,756.
U.S. Appl. No. 61/990,773.
U.S. Appl. No. 61/081,243, filed Nov. 18, 2014.
U.S. Appl. No. 15/129,222, filed Sep. 26, 2016.
U.S. Appl. No. 15/315,636, filed Dec. 1, 2016.
U.S. Appl. No. 15/752,991, filed Feb. 15, 2018.
U.S. Appl. No. 15/315,143, filed Apr. 27, 2018, Riedel et al.
U.S. Appl. No. 15/510,268, filed Mar. 10, 2017, Puhl et al.
U.S. Appl. No. 15/514,902, filed Mar. 28, 2017, BASF SE.
U.S. Appl. No. 15/521,921, filed Apr. 26, 2017.
U.S. Appl. No. 15/537,128, filed Jun. 16, 2017, Vautravers et al.
U.S. Appl. No. 15/744,324, filed Jan. 12, 2018, Parvulescu et al.
U.S. Appl. No. 15/744,474, filed Jan. 12, 2018, Rüdenauer et al.
U.S. Appl. No. 15/746,183, filed Jan. 19, 2018, BASF SE.
U.S. Appl. No. 15/746,082, filed Jan. 19, 2018, Gordillo et al.
U.S. Appl. No. 16/060,260, filed Jun. 7, 2018.
U.S. Appl. No. 15/766,425, filed Apr. 6, 2018, Thrun et al.
U.S. Appl. No. 15/753,236, filed Feb. 16, 2018.

* cited by examiner

TIN-CONTAINING ZEOLITIC MATERIAL HAVING A BEA FRAMEWORK STRUCTURE

CROSS-REFERENCE TO RELATED APPLICATIONS

This application is a national stage application (under 35 U.S.C. § 371) of PCT/EP2016/080015, filed Dec. 7, 2016, which claims benefit of European Application No. 15198365.7, filed Dec. 8, 2015, both of which are incorporated herein by reference in their entirety.

The present invention is directed to a novel process, in particular a wet-impregnation process for preparing a tin-containing zeolitic material having framework type BEA. Further, the present invention is directed to a novel tin-containing zeolitic material having framework type BEA which is preferably obtained by the novel process. Yet further, the present invention is directed to the use of the novel tin-containing zeolitic material having framework type BEA as a catalytically active material.

Zeolites having the framework type BEA (zeolite beta) doped with tin have shown promising results if used as catalytically active materials in certain applications such as Baeyer-Villiger-type oxidation reactions, isomerization reactions, and the like.

According to the known literature, tin containing zeolites having BEA framework structure are usually prepared by incorporation of tin into the zeolitic framework by hydrothermally treating a zeolitic material having vacant tetrahedral framework sites in the presence of tin-ion source. However, regarding this hydrothermal incorporation of tin, disadvantages have to be taken into account such as long synthesis time periods, the necessity to employ crystallization auxiliaries such as HF or cost intensive templating agents.

Hammond et al. describe a process for the preparation of zeolites having the framework type BEA which are prepared by incorporating tin into the zeolitic framework having vacant tetrahedral framework sites by a specific solid-state ion exchange process wherein said zeolitic framework having vacant tetrahedral framework sites is suitably mixed together with a solid tin-ion source. While the process described in Hammond et al. provides certain advantages compared to the previously known processes for the preparation of tin-containing zeolites having framework type BEA, the testing of the respectively obtained material in Baeyer-Villiger-type oxidation reactions which are explicitly mentioned in Hammond et al. did not show desired selectivities to the reaction product. Further, the process as such included certain reaction steps which, in particular in view of an industrial-scale process, are not necessarily a realistic option, such as the dealumination via an acid treatment.

Therefore, it was an object of the invention to provide tin-containing zeolitic material having framework type BEA exhibiting improved characteristics if used as a catalytically active material, in particular if used as catalytically active material in oxidation reactions such as Baeyer-Villiger-type oxidation reactions.

Thus, it was a further object of the invention to provide a novel process for the preparation of a tin-containing zeolitic material having framework type BEA comprising incorporating tin in a BEA framework structure having vacant tetrahedral sites via a simple process which, in particular, can be realized on an industrial scale.

A further object of the invention was to provide a tin-containing zeolitic material having framework type BEA with improved crystallinity and with lower amounts of extra-framework tin and bulk tin oxide.

Surprisingly, it was found that these objects can be achieved by subjecting a zeolitic material having framework type BEA having vacant tetrahedral sites to tin incorporation based on an aqueous mixture which comprises a tin-ion source and an acid.

Therefore, the present invention is directed to a process for preparing a tin-containing zeolitic material having framework type BEA, comprising (i) providing a zeolitic material having framework type BEA wherein the framework comprises $B_2O_3$ and $SiO_2$, wherein said framework has vacant tetrahedral framework sites;

(ii) providing a liquid aqueous mixture comprising a tin-ion source and an acid;

(iii) preparing a mixture of the zeolitic material provided in (i) and the aqueous mixture provided in (ii) obtaining a tin-containing zeolitic material having framework type BEA, wherein the ratio of the volume of the aqueous mixture divided by the mass of the zeolitic material, in $cm^3/g$, to the TPV is in the range of from 0.1:1 to 1.7:1, wherein the TPV is the total pore volume of the zeolitic material in $cm^3/g$ as determined by nitrogen absorption according to DIN 66134;

(iv) drying the zeolitic material obtained from (iii).

As mentioned above, it was found that starting from said zeolitic material having framework type BEA wherein the framework comprises $B_2O_3$ and $SiO_2$, wherein said framework has vacant tetrahedral framework sites, tin can be incorporated into said framework by a simple process, in particular a wet impregnation process, which is based on an aqueous mixture which comprises a suitable tin-ion source, and which involves subjecting the zeolitic material having framework type BEA wherein the framework comprises $B_2O_3$ and $SiO_2$, wherein said framework has vacant tetrahedral framework sites to said aqueous mixture. Obviously, preparing such an aqueous mixture, and treating a zeolitic material with such a mixture, is easily scalable to industrial-scale purposes.

In the context of the present invention, if the term "water" is used, this term preferably describes water having a conductivity of at most 50 microSiemens/cm.

Step (i)

According to step (i) of the process of the present invention, a zeolitic material is provided having framework type BEA comprising $B_2O_3$ and $SiO_2$, said framework having vacant tetrahedral framework sites.

Generally, no specific restrictions exist how this zeolitic material having vacant tetrahedral sites is provided. For example, it is conceivable to purchase a suitable, commercially available zeolitic material having vacant tetrahedral sites. Further, for example, any conceivable process for preparing such a zeolitic material can be employed for providing the zeolitic material. For example, it is conceivable to suitably synthesize a zeolitic material having BEA framework structure as a starting zeolitic material from suitable sources of $B_2O_3$ and $SiO_2$, either in the presence or in the absence of a suitable template compound, with or without making use of suitable seed crystals, for example in a hydrothermal synthesis process, and subject said starting zeolitic material, after optional washing and/or drying and/or calcining, to a suitable process stage wherein at least a portion of B is removed from the zeolitic framework and the vacant tetrahedral sites are formed. For example, at least a portion of B can be removed from the zeolitic framework by a treatment with steam and/or by a treatment with an acid.

For example in Hammond et al., it is described in the experimental section that aluminum is removed from the BEA zeolitic framework by treating the zeolitic material with a 13 M aqueous $HNO_3$ solution. In the context of the present invention, it was found that the zeolitic framework having the vacant tetrahedral sites is advantageously prepared by removing B from the zeolitic framework in a very mild process wherein neither steam nor an acid is used. In particular, it was found that B can be removed by treating the zeolitic starting material with a liquid solvent system, preferably under reflux, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic acid and does not contain an organic acid and does not contain a salt thereof, wherein more preferably, the liquid solvent system does not contain an inorganic acid having a pKa value of at most 5 and does not contain an organic acid having a pKa value of at most 5 and does not contain a salt thereof.

Preferably, according to (i), the zeolitic material having framework type BEA having vacant tetrahedral framework sites is provided by a method comprising (i.1) providing a zeolitic material having framework type BEA, wherein the framework of the zeolitic starting material comprises $B_2O_3$ and $SiO_2$ and the molar ratio $B_2O_3:SiO_2$ is greater than 0.02:1, preferably at least 0.03:1, more preferably in the range of from 0.03:1 to 0.07:1, more preferably from 0.03:1 to 0.06:1, more preferably from 0.03:1 to 0.05:1;

(i.2) creating vacant tetrahedral framework sites by treating the zeolitic material provided in (i.1) with a liquid solvent system, obtaining a zeolitic material having a molar ratio $B_2O_3:SiO_2$ of at most 0.02:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic and an organic acid and a salt thereof, and wherein the treating is preferably carried out at a temperature in the range of from 50 to 125° C., more preferably from 90 to 115° C., more preferably from 95 to 105° C., preferably for a period in the range of from 4 to 20 h, more preferably from 6 to 17 h, more preferably from 8 to 12 h;

(i.3) at least partially separating the zeolitic material obtained from (i.2) from the liquid solvent system, optionally including drying at a temperature of preferably less than 100° C.;

(i.4) optionally calcining the separated zeolitic material obtained from (i.3), preferably at a temperature in the range of from 400 to 700° C., more preferably from 450 to 550° C.

Also preferably, according to (i), the zeolitic material having framework type BEA having vacant tetrahedral framework sites is obtainable or obtained by a method comprising, preferably consisting of, (i.1) providing a zeolitic material having framework type BEA, wherein the framework of the zeolitic starting material comprises $B_2O_3$ and $SiO_2$ and the molar ratio $B_2O_3:SiO_2$ is greater than 0.02:1, preferably at least 0.03:1, more preferably in the range of from 0.03:1 to 0.07:1, more preferably from 0.03:1 to 0.06:1, more preferably from 0.03:1 to 0.05:1;

(i.2) creating vacant tetrahedral framework sites by treating the zeolitic material provided in (i.1) with a liquid solvent system, obtaining a zeolitic material having a molar ratio $B_2O_3:SiO_2$ of at most 0.02:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic or organic acid, or a salt thereof, and wherein the treating is preferably carried out at a temperature in the range of from 50 to 125° C., more preferably from 90 to 115° C., more preferably from 95 to 105° C., preferably for a period in the range of from 4 to 20 h, more preferably from 6 to 17 h, more preferably from 8 to 12 h;

(i.3) at least partially separating the zeolitic material obtained from (i.2) from the liquid solvent system, optionally including drying at a temperature of preferably less than 100° C.;

(i.4) optionally calcining the separated zeolitic material obtained from (i.3), preferably at a temperature in the range of from 400 to 700° C., more preferably from 450 to 550° C.

Step (i.1)

Generally, there are no specific restrictions how the zeolitic material having framework type BEA is provided in (i.1). For example, it may be conceivable to purchase a suitable, commercially available zeolitic material having framework type BEA. Further, for example, any conceivable process for synthesizing such a zeolite can be employed for providing the zeolitic material. Preferably, the zeolitic material is provided by a process starting from suitable sources of $B_2O_3$ and $SiO_2$ in the presence of a suitable template compound, also referred to as structure directing agent.

Generally, the framework structure of the zeolitic material provided in (i.1) comprises $B_2O_3$ and $SiO_2$. Preferably, the suitable sources of $B_2O_3$ and $SiO_2$ are employed in an amount so that at least 75 weight-%, more preferably at least 90 weight-%, more preferably at least 95 weight-%, more preferably at least 98 weight-%, more preferably at least 99 weight-% of the framework of the zeolitic material provided in (i.1) consist of $B_2O_3$ and $SiO_2$.

Generally, $B_2O_3$ and $SiO_2$ may be comprised in the zeolitic material having framework type BEA with a molar ratio $B_2O_3:SiO_2$ of greater than 0.02:1, preferably at least 0.03:1, more preferably in the range of from 0.03:1 to 0.07:1, more preferably from 0.03:1 to 0.06:1, more preferably from 0.03:1 to 0.05:1.

Therefore, a zeolitic material is preferably provided in (i.1), having framework type BEA, wherein at least 90 weight-%, more preferably at least 95 weight-%, more preferably at least 98 weight-%, more preferably at least 99 weight-% of the framework structure consists of $B_2O_3$ and $SiO_2$, and wherein the molar ratio $B_2O_3:SiO_2$ is greater than 0.02:1, more preferably at least 0.03:1, more preferably in the range of from 0.03:1 to 0.07:1, more preferably from 0.03:1 to 0.06:1, more preferably from 0.03:1 to 0.05:1. This material is also referred to as B-BEA.

Preferably, the zeolitic material provided in (i.1) is prepared by a synthetic method comprising (i.1.1) preparing a mixture comprising at least one template compound, at least one source for $SiO_2$ and at least one source for $B_2O_3$, and (i.1.2) crystallizing the zeolitic material from the mixture prepared in (i.1.1).

According to the present invention, the at least one template compound used in (i.1.1) can be any suitable template compound (structure directing agent). Suitable template compounds include tetraethylammonium hydroxide. Preferably, tetraethylammonium hydroxide is used.

Generally, the source for $SiO_2$ can be provided in (i.1.1) in any conceivable form, provided that a zeolitic material having framework type BEA comprising $SiO_2$ can be crystallized in (i.1.2). Preferably, $SiO_2$ is provided as such and/or as a compound which comprises $SiO_2$ as a chemical moiety and/or as a compound which, partly or entirely, is chemically transformed to $SiO_2$ during (i.1.2). Generally, all types of silica and silicates, preferably fumed silica, silica hydrosols, reactive amorphous solid silica, silica gel, silicic acid, water glass, sodium metasilicate hydrate, sesquisilicate or disilicate, colloidal silica, pyrogenic silica, silicic acid esters, or tetraalkoxysilanes, or mixtures of at least two of these compounds can be used. Preferably, said source for $SiO_2$ comprises at least one compound selected from the group consisting of silica and silicates, preferably silicates, more preferably alkali metal silicates. Among the preferred alkali metal silicates, the at least one source preferably comprises water glass, more preferably sodium and/or potassium silicate, more preferably sodium silicate. More preferably, the source for $SiO_2$ is sodium silicate. Fumed silica may be also preferred.

Generally, $B_2O_3$ can be provided in any conceivable form, provided that a zeolitic material having a framework type BEA comprising $B_2O_3$ can be crystallized in (i.1.2). Preferably, $B_2O_3$ is provided as such and/or as a compound which comprises $B_2O_3$ as a chemical moiety and/or as a compound which, partly or entirely, is chemically transformed to $B_2O_3$ during the inventive process. Preferably, free boric acid and/or borates and/or boric esters, such as, for example, triethyl borate, trimethyl borate, 2,4,6-trimethoxy boroxine, or 2,4,6-triethoxy boroxine, are used as starting materials and as the at least one source for $B_2O_3$.

Generally, the crystallization procedure according to (i.1.2) can be conducted in any conceivable manner, provided that a zeolitic material having framework type BEA is crystallized from the mixture according to (i.1.1). The mixture can be crystallized in any type of vessel, wherein a means of agitation is preferably employed, preferably by rotating the vessel or tumbling the vessel and/or stirring the mixture, more preferably by stirring the mixture.

Preferably, the mixture is heated during at least a portion of the crystallization process in (i.1.2). Generally, the mixture can be heated to any conceivable temperature of crystallization, provided that a zeolitic material having framework type BEA is crystallized from the mixture. Preferably, the mixture is heated to a temperature of crystallization in the range of from 80 to 200° C., more preferably from 90 to 190° C., more preferably from 100 to 185° C., more preferably from 120 to 180° C., more preferably from 140 to 175° C., more preferably from 150 to 165° C.

The preferred heating in (i.1.2) of the present invention can be conducted in any conceivable manner suitable for the crystallization of a zeolitic material having framework type BEA. Generally, the heating may be conducted at one temperature of crystallization or vary between different temperatures.

Generally, the duration of the crystallization process in (i.1.2) of the inventive process is not particularly limited. Preferably, the crystallization process is conducted for a period in the range of from 10 to 200 h, more preferably from 20 to 190 h, more preferably from 40 to 170 h, more preferably from 60 to 160 h, more preferably from 80 to 150 h, more preferably from 110 to 130 h.

Preferably, the heating in (i.1.2) is conducted during the entire crystallization process or during only one or more portions thereof, provided that a zeolitic material having framework type BEA is crystallized. Preferably, heating is conducted during the entire duration of crystallization.

Preferably, the crystallized material obtained from (i.1.2) is subjected to a sequence of isolation and/or washing steps, wherein the zeolitic material obtained from crystallization in (i.1.2) is preferably subjected to at least one isolation step and at least one washing step. Therefore, step (i.1) of the process of the present invention preferably comprises (i.1.1) preparing a mixture comprising at least one template compound, at least one source for $SiO_2$ and at least one source for $B_2O_3$, and (i.1.2) crystallizing the zeolitic material from the mixture prepared in (i.1.1);

(i.1.3) isolating and/or washing, preferably isolating and washing the crystallized material obtained from (i.1.2).

Isolation of the crystallized zeolitic material can be achieved by any conceivable method. These methods include, for example, filtration, ultrafiltration, diafiltration and centrifugation and/or decantation methods or, for instance, spray-drying processes and spray granulation processes, wherein filtration methods can involve suction and/or pressure filtration steps. A combination of two or more of these methods can be applied.

For the purpose of isolation, in particular filtration, the pH of the mother liquor obtained from (i.1.2) containing the crystallized zeolitic material is adjusted to a value in the range of from 6 to 9, preferably from 6.5 to 8.5, more preferably from 7 to 8, preferably by adding an acid to the mother liquor, preferably under stirring, wherein the adding of the acid is preferably carried out at a temperature of the mother liquor in the range of from 20 to 70° C., more preferably from 30 to 65° C., more preferably from 40 to 60° C. The acid is preferably an inorganic acid, preferably an aqueous solution containing the inorganic acid, wherein the inorganic acid is preferably selected from the group consisting of phosphoric acid, sulphuric acid, hydrochloric acid, nitric acid, and a mixture of two or more thereof, and wherein the inorganic acid is more preferably nitric acid.

With respect to one or more optional washing procedures, any conceivable solvent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, distilled water being very particularly preferred as the only washing agent.

The crystallized zeolitic material is preferably separated in (i.1.3) from the suspension obtained from (i.1.2) by filtration to obtain a filter cake which is preferably subjected to washing, preferably with water. If washing is applied, it is preferred to continue the washing process until the washing water has a conductivity of at most 1,000 microSiemens/cm, more preferably of at most 850 microSiemens/cm, more preferably of at most 700 microSiemens/cm.

Preferably, the zeolitic material obtained from (i.1.3) is subjected to a heat-treatment stage, wherein the zeolitic material obtained from (i.1.3) is preferably subjected pre-drying and/or drying and/or calcining. Therefore, step (i.1) of the process of the present invention preferably comprises (i.1.1) preparing a mixture comprising at least one template compound, at least one source for $SiO_2$ and at least one source for $B_2O_3$, and (i.1.2) crystallizing the zeolitic material from the mixture prepared in (i.1.1);

(i.1.3) isolating and/or washing, preferably isolating and washing the crystallized material obtained from (i.1.2);

(i.1.4) subjecting the zeolitic material obtained from (i.1.3) to a heat-treatment stage.

Optionally, the zeolitic material obtained from (i.1.3) is subjected to pre-drying, for example by subjecting the zeolitic material to a suitable gas stream such as air, lean air, or technical nitrogen, for a time preferably in the range of from 4 to 10 h, more preferably from 5 to 8 h.

The optionally the pre-dried filter cake is preferably dried. Preferably, drying is carried out at a temperature in the range of from 100 to 300° C., more preferably from 150 to 275° C., more preferably from 200 to 250° C. in a suitable atmosphere such as technical nitrogen, air, or lean air. Such drying can be accomplished, for example, in a suitable drying oven, or by spray-drying, wherein for spray-drying, a preferably aqueous suspension is preferably prepared from the optionally pre-dried filter cake. If the drying is accomplished by spray-drying, the drying gas inlet temperature is preferably in the range of from 200 to 250° C., more preferably from 220 to 250° C., and the drying gas outlet temperature is preferably in the range of from 100 to 175° C., more preferably from 120 to 150° C. If spray-drying is carried out, it is conceivable to subject the mother liquor obtained from (i.1.2) containing the zeolitic material, optionally after concentration, directly to spray-drying. Further, it is conceivable to subject the separated and washed zeolitic material to spray-drying, optionally after suitable re-suspending of the washed and optionally pre-dried zeolitic material wherein aqueous suspension are preferably prepared having preferred solids content range of from 2 to 35 weight-%, preferably from 5 to 25 weight-%, more preferably from 10 to 20 weight-%, based on the total weight of the suspension.

Preferably, the heat-treatment according to (i.1.4) comprises calcination of the zeolitic material wherein the zeolitic material is optionally subjected to spray-drying beforehand. Preferably, during calcination, the at least one template compound is at least partially, more preferably essentially removed from the framework structure. The calcination generally involves the heating of the zeolitic material to a temperature of at least 350° C., preferably to a temperature in the range of from 400 to 700° C., more preferably from 450 to 550° C. in a suitable atmosphere such as technical nitrogen, air, or lean air. Preferably, the calcination is carried out for a period in the range of from 1 to 10 h, preferably from 3 to 6 h. Thus, the calcination is preferably carried out at a temperature in the range of from 400 to 700° C., preferably from 450 to 550° C., for a period in the range of from 1 to 10 h, preferably from 3 to 6 h.

Therefore, the present invention relates to the process above, wherein step (i.1) comprises (i.1.1) preparing a mixture comprising at least one template compound, at least one source for $SiO_2$ and at least one source for $B_2O_3$;

(i.1.2) crystallizing the zeolitic material having from the mixture prepared in (i.1.1);

(i.1.3) isolating the zeolitic material obtained from (i.1.2) by filtration and washing the isolated zeolitic material;

(i.1.4) subjecting the isolated zeolitic material obtained from (i.1.3) to a heat-treatment stage preferably comprising pre-drying the zeolitic material, re-suspending the pre-dried zeolitic material, spray-drying the suspended zeolitic material, and calcining the spray-dried zeolitic material.

Step (i.2)

According to step (i.2) of the process of the present invention, vacant tetrahedral framework sites are created by treating the zeolitic starting material provided in (i.1) with a liquid solvent system. Preferably, the separated, spray-dried and calcined zeolitic material, provided in (i.1), is subjected to a treatment according to (i.2) with a liquid solvent system wherefrom a zeolitic material having a molar ratio $B_2O_3:SiO_2$ is obtained.

Generally, no specific restrictions exist concerning the chemical nature of the liquid solvent system used in (i.2). Thus, it is conceivable to use an acidic aqueous system for decreasing the molar ratio $B_2O_3:SiO_2$ of the zeolitic material to a value of at most 0.02:1. As acids, the liquid solvent system may comprise, for example, hydrochloric acid, sulfuric acid, nitric acid, phosphoric acid, formic acid, acetic acid, propionic acid, oxalic acid, or tartaric acid. Preferably, the liquid solvent system used in (i.2) is selected from the group consisting of water, monohydric alcohols, polyhydric alcohols, and mixtures of two or more thereof. Concerning the monohydric alcohols and polyhydric alcohols, no specific restrictions exist. Preferably, these alcohols contain from 1 to 6 carbon atoms, more preferably from 1 to 5 carbon atoms, more preferably from 1 to 4 carbon atoms, and more preferably from 1 to 3 carbon atoms. The polyhydric alcohols preferably comprise from 2 to 5 hydroxyl groups, more preferably from 2 to 4 hydroxyl groups, preferably 2 or 3 hydroxyl groups. Especially preferred monohydric alcohols are methanol, ethanol, and propanol like 1-propanol and 2-propanol. Especially preferred polyhydric alcohols are ethane-1,2-diol, propane-1,2-diol, propane-1,3-diol, propane-1,2,3-triol. If mixtures of two or more of above-described compounds are employed, it is preferred that these mixtures comprise water and at least one monohydric and/or at least one polyhydric alcohol. Most preferably, the liquid solvent system consists of water. Therefore, the present invention relates to above-defined process and zeolitic material obtainable or obtained therefrom, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water.

Further, it is especially preferred that the liquid solvent system does not contain an inorganic acid and an organic acid and a salt thereof, the acid being selected from the group consisting of hydrochloric acid, sulfuric acid, nitric acid, phosphoric acid, formic acid, acetic acid, propionic acid, oxalic acid, and tartaric acid. Therefore, the present invention also relates to the process above, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water, and wherein the liquid solvent system does not contain an inorganic acid and an organic acid and a salt thereof, the acid being selected from the group consisting of hydrochloric acid, sulfuric acid, nitric acid, phosphoric acid, formic acid, acetic acid, propionic acid, oxalic acid, and tartaric acid.

Even more preferably, the present invention also relates to the process above, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water, and wherein the liquid solvent system does not contain an inorganic acid and an organic acid and a salt thereof.

The reaction conditions according to (i.2) are not specifically restricted, provided that the solvent system described above is in its liquid state and that the molar ratio $B_2O_3$:$SiO_2$ is decreased to a value of at most 0.02:1. In particular, concerning the preferred temperatures described below, the skilled person will choose the respective pressure under which the treating is carried out in order to keep the solvent system in its liquid state. Concerning the duration of the treating according to (i.2), no specific restrictions exist. The above mentioned time is to be understood as the time where the liquid solvent system is maintained under the below described treating temperature. Preferably, in (i.2), the treating is carried out for a period of from 6 to 20 h, more preferably from 7 to 17 h, more preferably from 8 to 12 h. The preferred treating temperatures are in the range of from 50 to 125° C., preferably from 90 to 115° C., more preferably from 95 to 105° C. Most preferably, the treating according to (i.2) is carried out at the boiling point of the solvent system. If the solvent system is comprised of two or more components, the treating according to (i.2) is preferably carried out at the boiling point of the component having the lowest boiling point.

Preferably, the treating according to (i.2) is carried out under reflux. Thus, the preferred vessel, representing an open system, used for the treating according to (i.2) is preferably equipped with a reflux condenser. During the treating according to (i.2), the temperature of the liquid solvent system is kept essentially constant or changed, the treating with the liquid solvent system thus being carried out at two or more different temperatures. Most preferably, the temperature is kept essentially constant within the above-defined ranges.

Therefore, the present invention relates to the process above, comprising
(i.2) treating the zeolitic material provided in (i.1) with a liquid solvent system, preferably water, thereby obtaining a zeolitic material having a molar ratio $B_2O_3$:$SiO_2$, of at most 0.02:1 in an open system under reflux at a temperature in the range of from 95 to 105° C., and at least partially separating the zeolitic material from the liquid solvent system.

As far as the amount of zeolitic material which is employed relative to the amount of liquid solvent system, no specific restrictions exist. Preferably, the weight ratio of zeolitic material relative to the liquid solvent system is in the range of from 1:5 to 1:50, more preferably from 1:10 to 1:35, more preferably from 1:10 to 1:20, even more preferably from 1:12 to 1:18.

During treating according to (i.2), it is further preferred to suitably stir the liquid solvent system. During (i.2), the stirring rate is kept essentially constant or changed, the treating thus being carried out at two or more different stirring rates. Most preferably, the zeolitic material is suspended in the liquid solvent system at a first stirring rate, and during (i.2) at the above-described temperatures, the stirring rate is changed, preferably increased. The stirring rates as such can be suitably chosen depending, for example, on the volume of the liquid solvent system, the amount of the zeolitic material employed, the desired temperature, and the like. Preferably, the stirring rate under which the zeolitic material is suspended in the liquid solvent system is in the range of from 5 to 200 r.p.m. (revolutions per minute), more preferably from 10 to 200 r.p.m., more preferably from 20 to 55 r.p.m., more preferably from 30 to 50 r.p.m. The stirring rate under which the treating at the above-described temperatures is carried out is preferably in the range of from 50 to 100 r.p.m., more preferably from 55 to 90 r.p.m., more preferably from 60 to 80 r.p.m.

After the treating according to (i.2), the obtained zeolitic material is preferably separated from the liquid solvent system. Therefore, the present invention also relates to the process above, further comprising
(i.3) at least partially separating the zeolitic material obtained from (i.2) from the liquid solvent system, optionally including drying.

Step (i.3)

All methods of separating the zeolitic material from the liquid solvent system are conceivable. These methods include, for example, filtration, ultrafiltration, diafiltration and centrifugation methods or, for instance, spray-drying processes and spray granulation processes, wherein filtration methods can involve suction and/or pressure filtration steps. A combination of two or more of these methods can be applied.

With respect to one or more optional washing procedures, any conceivable solvent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, distilled water being very particularly preferred as the only washing agent. If washing as applied, it may be preferred to continue the washing process until the washing water has a conductivity of at most 1,000 microSiemens/cm, more preferably of at most 850 microSiemens/cm, more preferably of at most 700 microSiemens/cm.

According to the present invention, the zeolitic material is preferably separated from the suspension by filtration to obtain a filter cake which is preferably subjected to washing, preferably with water.

After separation of the zeolitic material having framework type BEA from the liquid solvent system, preferably achieved by filtration, and after washing, the zeolitic material obtained in (ii) is optionally subjected to drying. The drying procedure can optionally comprise one or more drying steps. In general, any conceivable means of drying can be used. Drying procedures preferably include heating and/or applying vacuum to the zeolitic material having framework type BEA.

Preferably, the separated and washed zeolitic material is subjected to pre-drying, for example by subjecting the filter cake to a suitable gas stream, such as air, lean air, or nitrogen, for a time preferably in the range of from 4 to 10 h, more preferably from 5 to 8 h.

Preferably, after the optional pre-drying, the zeolitic material is subjected to drying, preferably spray-drying wherein the drying gas inlet temperature is preferably in the range of from 200 to 250° C., more preferably from 220 to 250° C., and the drying gas outlet temperature is preferably in the range of from 100 to 175° C., more preferably from 120 to 150° C. If spray-drying is carried out, it is conceivable to subject the suspension containing the zeolitic material, optionally after concentration, directly to spray-drying. Further, it is conceivable to subject the separated and washed zeolitic material to spray-drying, preferably after suitable re-suspending of the washed and optionally pre-dried zeolitic material, preferably in de-ionized water. Preferably, the solid content of the aqueous suspension is in the range of from 2 to 35 weight-%, preferably from 5 to 25 weight-%, more preferably from 10 to 20 weight-%, based on the total weight of the suspension.

Preferably, the zeolitic material obtained from (i.3) is in the form of a powder, preferably in the form of a spray powder wherein the spray-powder may result either from spray-drying in (i.1) and/or spray-drying in (i.3).

Therefore, according to (i), the zeolitic material having framework type BEA having vacant tetrahedral framework sites is preferably provided by a method comprising (i.1) providing a zeolitic starting material having framework type BEA, wherein the framework structure of the zeolitic starting material comprises $B_2O_3$ and $SiO_2$ and the molar ratio $B_2O_3$ and $SiO_2$ is greater than 0.02:1, preferably at least 0.03:1, more preferably in the range of from 0.03:1 to 0.07:1, more preferably from 0.03:1 to 0.06:1, more preferably from 0.03:1 to 0.05:1;

(i.2) creating vacant tetrahedral framework sites by treating the zeolitic starting material provided in (i.1) with a liquid solvent system, preferably under reflux, obtaining a zeolitic material having a molar ratio $B_2O_3$ and $SiO_2$ of at most 0.02:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic acid and an organic acid and a salt thereof and wherein the treating is preferably carried out at a temperature in the range of from 50 to 125° C., more preferably from 90 to 115° C., more preferably from 95 to 105° C., and preferably for a period in the range of from 6 to 20 h, more preferably from 7 to 17 h, more preferably from 8 to 12 h;

(i.3) at least partially separating the zeolitic material obtained from (i.2) from the liquid solvent system, optionally including drying, preferably spray-drying.

According to the present invention, the separated zeolitic material obtained from (i.3) is optionally subjected to calcination in a step (i.4).

Step (i.4)

Preferably, the calcination according to (i.4) is carried out in a suitable atmosphere such as air, lean air, or nitrogen at a temperature in the range of from 400 to 700° C., preferably from 500 to 600° C., for a period in the range of from 1 to 10 h, preferably from 2 to 6 h.

Therefore, according to (i), the zeolitic material having framework type BEA having vacant tetrahedral framework sites is preferably provided by a method comprising (i.1) providing a zeolitic starting material having framework type BEA, wherein the framework structure of the zeolitic starting material comprises $B_2O_3$ and $SiO_2$ and the molar ratio $B_2O_3$ and $SiO_2$ is greater than 0.02:1, preferably at least 0.03:1, more preferably in the range of from 0.03:1 to 0.07:1, more preferably from 0.03:1 to 0.06:1, more preferably from 0.03:1 to 0.05:1;

(i.2) creating vacant tetrahedral framework sites by treating the zeolitic starting material provided in (i.1) with a liquid solvent system, preferably under reflux, obtaining a zeolitic material having a molar ratio $B_2O_3$ and $SiO_2$, of at most 0.02:1 wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic acid and an organic acid and a salt thereof, and wherein the treating is preferably carried out at a temperature in the range of from 50 to 125° C., more preferably from 90 to 115° C., more preferably from 95 to 105° C., and preferably for a period in the range of from 6 to 20 h, more preferably from 7 to 17 h, more preferably from 8 to 12 h;

(i.3) at least partially separating the zeolitic material obtained from (i.2) from the liquid solvent system, optionally including drying, preferably spray-drying;

(i.4) optionally calcining the separated zeolitic material obtained from (i.3), preferably at a temperature in the range of from 400 to 700° C., more preferably from 450 to 550° C., and preferably for a time period in the range of from 1 to 10 h, more preferably from 3 to 6 h.

Preferably, the zeolitic material obtained in (i.3) is not subjected to calcination prior to (iii).

Therefore, according to (i), the zeolitic material having a framework type BEA having vacant tetrahedral framework sites is preferably provided by a method comprising (i.1) providing a zeolitic starting material having framework type BEA, wherein the framework structure of the zeolitic starting material comprises $B_2O_3$ and $SiO_2$ and the molar ratio $B_2O_3$ and $SiO_2$ is greater than 0.02:1, preferably at least 0.03:1, more preferably in the range of from 0.03:1 to 0.07:1, more preferably from 0.03:1 to 0.06:1, more preferably from 0.03:1 to 0.05:1;

(i.2) creating vacant tetrahedral framework sites by treating the zeolitic starting material provided in (i.1) with a liquid solvent system, preferably under reflux, obtaining a zeolitic material having a molar ratio $B_2O_3$ and $SiO_2$ of at most 0.02:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic acid and an organic acid and a salt thereof, and wherein the treating is preferably carried out at a temperature in the range of from 50 to 125° C., more preferably from 90 to 115° C., more preferably from 95 to 105° C., and preferably for a period in the range of from 6 to 20 h, more preferably from 7 to 17 h, more preferably from 8 to 12 h;

(i.3) at least partially separating the zeolitic material obtained from (i.2) from the liquid solvent system, preferably including drying, preferably spray-drying, wherein after (i.3) and before (iii), the preferably dried, more preferably spray-dried zeolitic material is not subjected to calcination at a temperature in the range of from 450 to 550° C. and a time period in the range of from 3 to 6 h, preferably not subjected to calcination at a temperature in the range of from 400 to 700° C. and a time period in the range of from 1 to 10 h, more preferably not subjected to calcination.

According to the present invention, the treatment according to (i.2) with the liquid solvent system decreases the molar ratio $B_2O_3:SiO_2$ of the zeolitic material; thus, it is a procedure for removing at least a portion of B from the BEA framework structure and creating vacant tetrahedral sites in the zeolitic framework. According to a preferred embodiment of the present invention, the molar ratio $B_2O_3:SiO_2$ of the zeolitic material obtained in (i.2), preferably in (i.3), is at most 0.02:1, preferably at most 0.01:1, more preferably in the range of from 0.0005:1 to 0.01:1, more preferably from 0.0009:1 to 0.003:1.

It is especially preferred that the zeolitic material having framework type BEA is free of aluminum. The term "free of aluminum" as used in this context of the present invention relates to a zeolitic material having BEA framework structure which may contain aluminum only in traces as impurities which may result, for example, from aluminum impurities in the starting materials present in the synthesis mixture used for the preparation of the zeolitic material, that is as impurities in the silicon source, the boron source, the template compound, and the water. In particular, no aluminum source is used in the synthesis mixture in (i.1).

Preferably, at least 95 weight-%, preferably at least 98 weight-%, more preferably at least 99 weight-% of the framework structure of the zeolitic material provided in (i) consist of B, Si, O, and H. More preferably, at least 99.5 weight-%, more preferably at least 99.8 weight-%, more preferably at least 99.9 weight-% of the framework structure of the zeolitic material provided in (i) consist of B, Si, O, and H.

Based on the composition of the zeolitic material having BEA framework structure which is subjected to the removal of X, preferably B, from the zeolitic framework, and further based on the composition of the zeolitic material having BEA framework structure obtained from the removal of X, preferably B, from the zeolitic framework, the molar amount of the vacant tetrahedral framework sites formed by the removal stage can be easily calculated.

Step (ii)

According to step (ii) of the process of the present invention, a liquid aqueous mixture comprising a tin-ion source and an acid is provided.

Regarding the tin-ion source, no specific restrictions exist provided that based on the respectively prepared aqueous mixture, the treatment according to (iii) can be carried out. Preferably, the tin-ion source according to (ii) is one or more of tin(II) alkoxides, tin(IV) alkoxides, tin(II) salts of organic acids, tin(IV) salts of organic acids. More preferably, the tin-ion source is one or more of tin(II) alkoxides having from 1 to 4 carbon atoms such as 1 carbon atom, 2 carbon atoms, 3 carbon atoms, or 4 carbon atoms, tin(IV) alkoxides having from 1 to 4 carbon atoms such as 1 carbon atom, 2 carbon atoms, 3 carbon atoms, or 4 carbon atoms, tin(II) salts of organic acids having from 1 to 6 carbon atoms such as 1 carbon atom, 2 carbon atoms, 3 carbon atoms, 4 carbon atoms, 5 carbon atoms, or 6 carbon atoms, tin(IV) salts of organic acids having from 1 to 6 carbon atoms such as 1 carbon atom, 2 carbon atoms, 3 carbon atoms, 4 carbon atoms, 5 carbon atoms, or 6 carbon atoms, and a mixture a two or more thereof. More preferably, the tin-ion source includes a tin(II) salt of organic acids having from 1 to 6 carbon atoms such as 1 carbon atom, 2 carbon atoms, 3 carbon atoms, 4 carbon atoms, 5 carbon atoms, or 6 carbon atoms, or a tin(IV) salt of organic acids having from 1 to 6 carbon atoms such as 1 carbon atom, 2 carbon atoms, 3 carbon atoms, 4 carbon atoms, 5 carbon atoms, or 6 carbon atoms. More preferably, the tin-ion source includes a tin(II) salt of organic acids having from 1 to 6 carbon atoms such as 1 carbon atom, 2 carbon atoms, 3 carbon atoms, 4 carbon atoms, 5 carbon atoms, or 6 carbon atoms. More preferably, the tin-ion source comprises, more preferably consists of, tin(II) acetate.

Regarding the acid comprised in the liquid aqueous mixture provided in (ii), no specific restrictions exist provided that based on the respectively prepared aqueous mixture, the treatment according to (iii) can be carried out. Preferably, the acid comprised in the liquid aqueous mixture provided in (ii) is one or more organic acids, or one or more inorganic acids, or one or more organic acids and one or more inorganic acids. More preferably, if the one or more acids is one or more organic acids, the one or more organic acids is one or more of acetic acid, oxalic acid, and citric acid. More preferably, if the one or more acids is one or more inorganic acids, the one or more inorganic acids is one or more of phosphoric acid, sulphuric acid, hydrochloric acid, nitric acid, and methane sulfonic acid. More preferably, the acid comprised in the liquid aqueous mixture provided in (ii) comprises, preferably consists of, acetic acid.

According to the present invention, it is preferred that the liquid aqueous mixture comprises the acetic acid in an amount in the range of from 2 to 43 weight-%, preferably in the range of from 10 to 40 weight-%, more preferably in the range of from 15 to 35 weight-%, based on the amount of the liquid aqueous mixture. Preferably, the liquid aqueous mixture provided in (ii) has a pH in the range of from 1 to 5, more preferably in the range of from 1 to 4, more preferably in the range of from 1 to 3, more preferably in the range of from 1 to 2, as determined via a pH sensitive glass electrode.

According to the present, it is preferred that the liquid aqueous mixture provided in (ii) comprises the tin-ion source, calculated as elemental Sn, in an amount in the range of from 1 to 25 weight-%, preferably in the range of from 1.2 to 22 weight-%, more preferably in the range of from 1.5 to 19 weight-%, based on the amount of water comprised in the acidic liquid aqueous mixture. Preferred ranges are, for example, from 1.5 to 4 weight-% or from 4 to 6.5 weight-% or from 6.5 to 9 weight-% or from 9 to 11.5 weight-% or from 11.5 to 14 weight-% or from 14 to 16.5 weight-% or from 16.5 to 19 weight-%, based on the amount of water comprised in the acidic liquid aqueous mixture.

Generally, it is conceivable that in addition to the water, the tin-ion source and the acid, the liquid aqueous mixture provided in (ii) comprises one or more further compounds provided that the process of the present invention can be carried out. Preferably, at least 95 weight-%, more preferably at least 98 weight-%, more preferably at least 99 weight-% of the acidic liquid aqueous mixture provided in (ii) consist of the tin-ion source, the acid, and water. More preferably, the liquid aqueous mixture provided in (ii) essentially consists of the water, the tin-ion source and the acid wherein the term "essentially consists of" as used in this context relates to a liquid aqueous mixture of which more than 99 weight-% consist of the water, the tin-ion source and the acid.

Step (iii)

According to (iii), a mixture of the zeolitic material provided in (i) and the aqueous mixture provided in (ii) is prepared, wherein the ratio of the volume of the aqueous mixture divided by the mass of the zeolitic material, in $cm^3/g$, to the TPV is in the range of from 0.1:1 to 1.7:1, wherein the TPV is the total pore volume of the zeolitic material in $cm^3/g$ as determined by nitrogen absorption according to DIN 66134, obtaining a tin-containing zeolitic material having framework type BEA. In particular, according to (iii), a mixture of the zeolitic material provided in (i) and the aqueous mixture provided in (ii) is prepared, wherein the ratio of the volume of the aqueous mixture divided by the mass of the zeolitic material, in cm$^3$/g, to the TPV is in the range of from 0.1:1 to 1.7:1, wherein the TPV is the total pore volume of the zeolitic material in cm$^3$/g as determined by nitrogen absorption according to DIN 66134, obtaining a tin-containing zeolitic material having framework type BEA, wherein the total pore volume TPV is determined by converting the adsorbed nitrogen gas volume at a relative pressure of p/p$_0$=0.99 according to the nitrogen adsorption as determined according to DIN 66134 into the corresponding liquid volume using a gaseous nitrogen density of 1.25×10$^3$ g/cm$^3$ and a liquid nitrogen density of 0.81 g/cm$^3$ at a temperature of 25° C. and an absolute pressure of 1 bar.

Preferably, in (iii), the ratio of the volume of the aqueous mixture divided by the mass of the zeolitic material, in cm$^3$/g, to the TPV is in the range of from 0.2:1 to 1.6:1, preferably in the range of from 0.4:1 to 1.5:1, more preferably in the range of from 0.6:1 to 1.4:1. Preferred ranges are, for example, from 0.7:1 to 1.4:1 or from 0.8:1 to 1.4:1.

Preferably, preparing the mixture according to (iii) comprises agitating the mixture, more preferably mechanically agitating the mixture, more preferably stirring the mixture. The term "agitation" as used in this context of the present invention relates to any motion of a macroscopic constituent of the mixture which is induced from outside, relative to another macroscopic constituent of the mixture. The term "mechanical agitation" as used in this context of the present invention relates to any motion of a macroscopic constituent of the mixture which is induced from outside via a device, such as shaking or stirring or sonication, relative to another macroscopic constituent of the mixture. The term "stirring" as used in this context of the present invention relates to any motion of a macroscopic constituent of the mixture which is induced from outside via a stirring device, relative to another macroscopic constituent of the mixture.

The temperature of the mixture according to (iii), preferably the temperature of the mixture during agitating as mentioned above, is preferably above 0° C. and preferably below 90° C. More preferably, the temperature is in the range of from 1 to 75° C., preferably in the range of from 2 to 60° C., more preferably in the range of from 5 to 50° C. More preferably, according to (iii), the mixture is prepared at a temperature of the mixture in the range of from 10 to 40° C., preferably in the range of from 15 to 35° C., more preferably in the range of from 20 to 30° C.

The absolute pressure under which the mixture according to (iii) is prepared, preferably the absolute pressure under which the mixture is agitated as mentioned above, is preferably in the range of from 0.1 to 5 bar, preferably in the range of from 0.2 to 4 bar, more preferably in the range of from 0.3 to 3 bar. More preferably, the absolute pressure is in the range of from 0.5 to 2 bar, more preferably in the range of from 0.8 to 1.2 bar, more preferably in the range of from 0.9 to 1.1 bar.

Therefore, it is preferred that according to (iii), a mixture of the zeolitic material provided in (i) and the aqueous mixture provided in (ii) is prepared, wherein the ratio of the volume of the aqueous mixture divided by the mass of the zeolitic material, in cm$^3$/g, to the TPV is in the range of from 0.6:1 to 1.4:1, wherein the TPV is the total pore volume of the zeolitic material in cm$^3$/g as determined by nitrogen absorption according to DIN 66134, obtaining a tin-containing zeolitic material having framework type BEA, wherein preparing the mixture comprises agitating, preferably stirring the mixture at a temperature of the mixture in the range of from 10 to 40° C. and at an absolute pressure in the range of from 0.5 to 2 bar.

Step (iv)

According to (iv), the mixture obtained from (iii) comprising a tin-containing zeolitic material having framework type BEA, in particular the tin-containing zeolitic material having framework type BEA obtained from the impregnation according to (iii), is subjected to suitable drying, to obtain a dried tin-containing zeolitic material having framework type BEA.

Generally, it is possible to dry the tin-containing zeolitic material having framework type BEA obtained from the impregnation according to (iii) in an atmosphere which is essentially free of oxygen, such as in an argon atmosphere, a nitrogen atmosphere, or the like, or in an atmosphere comprising oxygen, such as in oxygen, air lean air, or the like. It is also possible to dry the tin-containing zeolitic material having framework type BEA obtained from the impregnation according to (iii) in an atmosphere which is essentially free of oxygen, such as in an argon atmosphere, a nitrogen atmosphere, or the like, and, either after or prior to drying in the atmosphere which is essentially free of oxygen, to dry it in an atmosphere comprising oxygen, such as in oxygen, air lean air, or the like. Preferably, according to (iv), the zeolitic material is dried in a first drying period in an atmosphere which is essentially free of oxygen, preferably nitrogen, and wherein in a second drying period, the respectively dried zeolitic material is further dried in an atmosphere comprising oxygen, preferably air or lean air, more preferably air.

The temperature of the drying atmosphere is not subject to any specific restrictions. Preferably, according to (iv), the zeolitic material is dried at a temperature, preferably of a temperature of the drying atmosphere in the range of from 10 to 90° C., more preferably in the range of from 20 to 90° C., more preferably in the range of from 30 to 90° C. More preferably, according to (iv), the zeolitic material is dried at a temperature, preferably of a temperature of the drying atmosphere in the range of from 40 to 90° C., preferably in the range of from 50 to 80° C., more preferably in the range of from 60 to 70° C. If two or more different drying atmospheres are used in two or more subsequent drying stages, the temperatures of the respective drying stages can be the same or different and are preferably in the above-defined preferred ranges. Therefore, if two different drying atmospheres are used, it is preferred that according to (iv), the zeolitic material is dried at temperatures of the drying atmospheres in the range of from 10 to 90° C., more preferably in the range of from 20 to 90° C., more preferably in the range of from 30 to 90° C. More preferably, according to (iv), the zeolitic material is dried at temperatures of the drying atmospheres in the range of from 40 to 90° C., preferably in the range of from 50 to 80° C., more preferably in the range of from 60 to 70° C.

Therefore, it is preferred that according to (iii), a mixture of the zeolitic material provided in (i) and the aqueous mixture provided in (ii) is prepared, wherein the ratio of the volume of the aqueous mixture divided by the mass of the zeolitic material, in cm$^3$/g, to the TPV is in the range of from 0.6:1 to 1.4:1, wherein the TPV is the total pore volume of the zeolitic material in cm$^3$/g as determined by nitrogen absorption according to DIN 66134, obtaining a tin-containing zeolitic material having framework type BEA, wherein preparing the mixture comprises agitating, preferably stirring the mixture at a temperature of the mixture in the range of from 10 to 40° C. and at an absolute pressure in the range of from 0.5 to 2 bar, and wherein the mixture obtained from (iii), and thus the tin-containing zeolitic material having framework type BEA comprised in said mixture, is subjected to drying according to (iv) in a first drying period in an atmosphere which is essentially free of oxygen, preferably nitrogen, and wherein in a second drying period, the respectively dried zeolitic material dried is further dried in an atmosphere comprising oxygen, preferably air or lean air, more preferably air, wherein the temperature of the drying atmospheres are in the range of from 40 to 90° C.

The drying can be carried, for example, in a conventional drying oven, and/or using a suitable rapid-drying method such as spray-drying, spray-granulation, or flash-drying. If, for example, spray-drying is used, a spray-powder is obtained from the drying wherein the particles of the powder consist of an agglomeration of the crystals of the zeolitic material obtained from (iii). If, for example, spray-granulation is used, a spray-granulate is obtained from the drying wherein the granules comprise the crystals of the zeolitic material obtained from (iii).

Step (v)

According to (v), the dried zeolitic material obtained from (iv) is preferably calcined.

Generally, it is possible to calcined the dried tin-containing zeolitic material having framework type BEA obtained from (iv) in an atmosphere which comprises nitrogen, such as in nitrogen, air, lean air, or the like. It is also possible to calcined the dried tin-containing zeolitic material having framework type BEA obtained from (iv) in an atmosphere which is essentially free of oxygen, such as in an argon atmosphere, a nitrogen atmosphere, or the like, and, either after or prior to calcining in the atmosphere which is essentially free of oxygen, to calcined it in an atmosphere comprising oxygen, such as in oxygen, air lean air, or the like. Preferably, according to (v), the zeolitic material is calcined in a first calcining period in an atmosphere which comprises nitrogen, and wherein in a further calcining period, the respectively calcined zeolitic material is further calcined in an atmosphere comprising oxygen, preferably air or lean air, more preferably air.

The temperature of the calcining atmosphere is not subject to any specific restrictions. Preferably, according to (iv), the zeolitic material is dried at a temperature, preferably of a temperature of the calcining atmosphere in the range of from 350 to 650° C., more preferably in the range of from 400 to 600° C., more preferably in the range of from 450 to 550° C. If two or more different calcining atmospheres are used in two or more subsequent calcining stages, the temperatures of the respective calcining stages can be the same or different and are preferably in the above-defined preferred ranges. Therefore, if two different calcining atmospheres are used, it is preferred that according to (v), the dried zeolitic material is calcined at temperatures of the calcining atmospheres in the range of from 350 to 650° C., more preferably in the range of from 400 to 600° C., more preferably in the range of from 350 to 550° C.

Generally, the period of time for which the dried zeolitic material is calcined can be adjusted to the specific needs. Generally, the dried zeolitic material is calcined for a period of time in the range of from 0.1 to 96 h such as from 0.2 to 72 h or from 0.5 to 48 h. Preferred ranges can be from 1 to 24 h, more preferably in the range of from 2 to 18 h, more preferably in the range of from 3 to 12 h. Preferably, the dried zeolitic material is calcined until the total organic carbon (TOC) content of the zeolitic material is at most 0.2 weight-%, based on the total weight of the zeolitic material.

Step (vi)

From said drying or calcining, the tin-containing zeolitic material having framework type BEA is usually obtained in the form of a powder, such as the powder consisting of the crystals of the tin-containing zeolitic material having framework type BEA, or consisting of a spray-powder which in turn consists of an agglomeration of crystals of the tin-containing zeolitic material having framework type BEA, or consisting of a spray-granulate which in turn comprises an agglomeration of crystals of the tin-containing zeolitic material having framework type BEA.

In a step further optional step (vi), it may be preferred, depending, for example, of the use of the tin-containing zeolitic material having framework type BEA, to further shape the tin-containing zeolitic material having framework type BEA to obtain suitable moldings. Conceivable shaping may include, for example, rapid-drying including spray-drying or spray-granulation. It is possible, for example, that said rapid-drying is carried out using a binder, such a silica binder, or precursor of a binder, obtaining the moldings, preferably the spray-granules which comprise the tin-containing zeolitic material having framework type BEA and the binder.

Based on said moldings obtained from (vi), or also based on the powder obtained from (iv) or (v), it is further possible to calcine said moldings or said powder in a further step (vii), wherein one or more suitable post-treatment steps may follow, such as a water-treatment under suitable conditions in a step (viii) wherein the post-treated zeolitic material may be further dried and/or calcined in a step (ix). Therefore, the process of the present invention may further comprise one or more of:

(vii) calcining the moldings, preferably the spray-granules, obtained from (vi)

(viii) subjecting the moldings, preferably the spray-granules, obtained from (vii), or the powder obtained from (iv) or (vi), preferably (v), to a water-treatment, wherein the water-treatment comprises treating the molding or the powder with liquid water in an autoclave under autogenous pressure at a temperature in the range of from 100 to 200° C.;

(ix) drying and/or calcining the water-treated molding, preferably the spray-granules, or the water-treated powder obtained from (viii).

The Tin-Containing Zeolitic Material as Such

The present invention further relates to a tin-containing zeolitic material having framework type BEA comprising $B_2O_3$ and $SiO_2$, wherein the framework additionally comprises tin, wherein in the framework structure of the zeolitic material, the molar ratio $B_2O_3:SiO_2$ is at most 0.02:1, preferably at most 0.01:1, more preferably in the range of from 0.0005:1 to 0.01:1, more preferably from 0.0009:1 to 0.003:1, wherein at least 95 weight-%, preferably at least 98 weight-%, more preferably at least 99 weight-% of the framework of the zeolitic material consist of Si, B, O, H. For example, said tin-containing zeolitic material having framework type BEA is obtainable or obtained by process as described hereinabove.

Surprisingly, it was found that the novel tin-containing zeolitic material is characterized by a very high crystallinity. Since the novel tin-containing zeolitic material is suitable, for example, as a catalytically active material in chemical reactions, this very high crystallinity is of particular importance since a very high crystallinity means that a very high active mass of catalytically active material is present.

Therefore, the present invention also relates to a tin-containing zeolitic material having framework type BEA comprising $B_2O_3$ and $SiO_2$, wherein the framework additionally comprises tin, wherein in the framework structure of the zeolitic material, the molar ratio $B_2O_3:SiO_2$ is at most 0.02:1, preferably at most 0.01:1, more preferably in the range of from 0.0005:1 to 0.01:1, more preferably from 0.0009:1 to 0.003:1, wherein at least 95 weight-%, preferably at least 98 weight-%, more preferably at least 99 weight-% of the framework of the zeolitic material consist of Si, B, O, H, and tin, said tin-containing zeolitic material having framework type BEA having a crystallinity, as determined via XRD according to Reference Example 5, in the range of from 55 to 80%, preferably in the range of from 60 to 70%, and having BET specific surface area determined according to DIN 66131 of at least 400 m²/g, preferably in the range of from 400 to 600 m²/g. More preferred ranges of the BET specific surface area arte, for example, from 410 to 580 m²/g or from 420 to 560 m²/g or from 430 to 540 m²/g.

The novel tin-containing zeolitic material is further preferably characterized by a specific UV-VIS spectrum. In particular, the ratio of the intensity of the maximum absorption peak which is in the range of from 200 to 220 relative to the intensity of the shoulder which is in the range of from 245 to 260 nm to is in the range of from 2.1 to 8.0, preferably in the range of from 2.3 to 7.0, more preferably in the range of from 2.5 to 6.0. This parameter is a clear indication that only a very low amount of extra-framework tin is comprised in the zeolitic materials according to the invention. This means that the zeolitic materials according to the invention have a very high number of catalytically active sites.

Preferably, the novel tin-containing zeolitic material has a tin content in the range of from 0.5 to 20 weight-%, preferably in the range of from 2 to 18 weight-%, based on the total weight of the tin-containing zeolitic material. Preferred ranges include, for example, from 2 to 6 weight-% or from 4 to 8 weight-% or from 6 to 10 weight-% or from 8 to 12 weight-% or from 10 to 14 weight-% or from 12 to 16 weight-% or from 14 to 18 weight-%.

The novel tin-containing zeolitic material may be either a zeolitic powder essentially constituted by the crystals of the zeolitic material. Further, said powder may be comprised in molding which may further comprise a binder such as a silica binder. Such moldings can be, for examples, spray-powders, spray-granules, extrudates, tablets, or the like.

Uses

Generally, no specific restrictions exist as to possible uses of the novel tin-containing zeolitic material. The use as a catalytically active material may be mentioned as preferred use, more preferably as a catalytically active material in oxidation reactions including Baeyer-Villiger-type oxidation reactions, Dakin-type reactions and Oppenauer-type oxidation reactions, reduction reactions including Meerwein-Ponndorf-Verley-type reduction reactions, aldol condensation reactions, retro-aldol reactions including the reaction of glucose to lactic acid, isomerization reactions including the isomerization of glucose to fructose. A preferred use is, for example, the use as a catalytically active material in Baeyer-Villiger-type oxidation reactions, such as in a Baeyer-Villiger-type reaction for preparing a compound of formula (III)

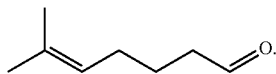
(III)

This Baeyer-Villiger-type reaction preferably comprises
(a) oxidizing a compound of formula (I)

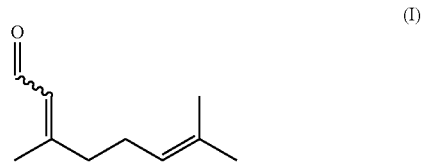
(I)

with hydrogen peroxide in the presence of the tin-containing zeolitic material having framework type BEA or in the presence of the molding comprising the tin-containing zeolitic material having framework type BEA, obtaining a reaction mixture comprising a compound of formula (II)

(II)

and optionally the compound of formula (III), wherein in (a), preferably more than 50%, more preferably at least 95% of the compound of formula (I) are present as compound of formula (Ia)

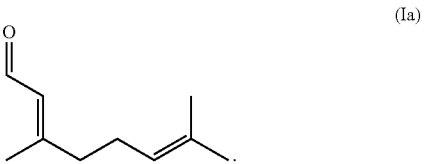
(Ia)

The present invention is further illustrated by the following first set of embodiments and combinations of embodiments resulting from the given dependencies and back-references.

1. A process for preparing a tin-containing zeolitic material having framework type BEA, comprising
   (i) providing a zeolitic material having framework type BEA wherein the framework comprises $B_2O_3$ and $SiO_2$, wherein said framework has vacant tetrahedral framework sites;
   (ii) providing a liquid aqueous mixture comprising a tin-ion source and an acid;
   (iii) preparing a mixture of the zeolitic material provided in (i) and the aqueous mixture provided in (ii) obtaining a tin-containing zeolitic material having framework type BEA, wherein the ratio of the volume of the aqueous mixture divided by the mass of the zeolitic material, in cm³/g, to the TPV is in the range of from 0.1:1 to 1.7:1, wherein the TPV is the total pore volume of the zeolitic material in cm³/g as determined by nitrogen absorption according to DIN 66134;
   (iv) drying the zeolitic material obtained from (iii).
2. The process of embodiment 1, wherein the ratio of the volume of the aqueous mixture divided by the mass of the zeolitic material, in cm³/g, to the TPV is in the range of from 0.2:1 to 1.6:1, preferably in the range of from 0.4:1 to 1.5:1, more preferably in the range of from 0.6:1 to 1.4:1.
3. The process of embodiment 1 or 2, wherein the ratio of the volume of the aqueous mixture divided by the mass of the zeolitic material, in cm³/g, to the TPV is in the range of from 0.8:1 to 1.4:1.
4. The process of any one of embodiments 1 to 3, wherein the total pore volume TPV is determined by converting the adsorbed nitrogen gas volume at a relative pressure of $p/p_0=0.99$ according to the nitrogen adsorption as determined according to DIN 66134 into the corresponding liquid volume using a gaseous nitrogen density of 1.25×10$^3$ g/cm$^3$ and a liquid nitrogen density of 0.81 g/cm$^3$ at a temperature of 25° C. and an absolute pressure of 1 bar.

5. The process of any one of embodiments 1 to 4, wherein according to (i), the zeolitic material having framework type BEA having vacant tetrahedral framework sites is provided by a method comprising
   (i.1) providing a zeolitic material having framework type BEA, wherein the framework of the zeolitic starting material comprises B$_2$O$_3$ and SiO$_2$ and the molar ratio B$_2$O$_3$:SiO$_2$ is greater than 0.02:1, preferably at least 0.03:1, more preferably in the range of from 0.03:1 to 0.07:1, more preferably from 0.03:1 to 0.06:1, more preferably from 0.03:1 to 0.05:1;
   (i.2) creating vacant tetrahedral framework sites by treating the zeolitic material provided in (i.1) with a liquid solvent system, obtaining a zeolitic material having a molar ratio B$_2$O$_3$:SiO$_2$ of at most 0.02:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic acid and an organic acid and a salt thereof, and wherein the treating is preferably carried out at a temperature in the range of from 50 to 125° C., more preferably from 90 to 115° C., more preferably from 95 to 105° C., preferably for a period in the range of from 4 to 20 h, more preferably from 6 to 17 h, more preferably from 8 to 12 h;
   (i.3) at least partially separating the zeolitic material obtained from (i.2) from the liquid solvent system, optionally including drying;
   (i.4) optionally calcining the separated zeolitic material obtained from (i.3), preferably at a temperature in the range of from 400 to 700° C., more preferably from 450 to 550° C.

6. The process of any one of embodiments 1 to 4, wherein according to (i), the zeolitic material having framework type BEA having vacant tetrahedral framework sites is obtainable or obtained by a method comprising, preferably consisting of,
   (i.1) providing a zeolitic material having framework type BEA, wherein the framework of the zeolitic starting material comprises B$_2$O$_3$ and SiO$_2$ and the molar ratio B$_2$O$_3$:SiO$_2$ is greater than 0.02:1, preferably at least 0.03:1, more preferably in the range of from 0.03:1 to 0.07:1, more preferably from 0.03:1 to 0.06:1, more preferably from 0.03:1 to 0.05:1;
   (i.2) creating vacant tetrahedral framework sites by treating the zeolitic material provided in (i.1) with a liquid solvent system, obtaining a zeolitic material having a molar ratio B$_2$O$_3$:SiO$_2$ of at most 0.02:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic acid and an organic acid and a salt thereof, and wherein the treating is preferably carried out at a temperature in the range of from 50 to 125° C., more preferably from 90 to 115° C., more preferably from 95 to 105° C., preferably for a period in the range of from 4 to 20 h, more preferably from 6 to 17 h, more preferably from 8 to 12 h;
   (i.3) at least partially separating the zeolitic material obtained from (i.2) from the liquid solvent system, optionally including drying;
   (i.4) optionally calcining the separated zeolitic material obtained from (i.3), preferably at a temperature in the range of from 400 to 700° C., more preferably from 450 to 550° C.

7. The process of embodiment 5 or 6, wherein providing a zeolitic material having framework type BEA according to (i.1) comprises
   (i.1.1) preparing a mixture comprising at least one BEA template compound, at least one source for SiO$_2$ and at least one source for B$_2$O$_3$;
   (i.1.2) crystallizing the zeolitic material from the mixture prepared in (i.1.1);
   (i.1.3) isolating and/or washing, preferably isolating and washing the crystallized material obtained from (i.1.2);
   (i.1.4) subjecting the zeolitic material obtained from (i.1.3) to a heat-treatment stage.

8. The process of any one of embodiments 5 to 7, wherein creating vacant tetrahedral framework sites according to (i.2) comprises
   (i.2) treating the zeolitic material provided in (i.1) with a liquid solvent system, preferably water, thereby obtaining a zeolitic material having a molar ratio B$_2$O$_3$:SiO$_2$, of at most 0.02:1 in an open system at a temperature in the range of from 95 to 105° C.

9. The process of any one of embodiments 5 to 8, wherein at least partially separating the zeolitic material according to (i.3) comprises
   (i.3) at least partially separating the zeolitic material obtained from (i.2) from the liquid solvent system including drying, preferably spray-drying.

10. The process of any one of embodiments 5 to 9, wherein the zeolitic material obtained from (i.3) is not subjected to calcination prior to (iii).

11. The process of any one of embodiments 1 to 10, wherein in the framework of the zeolitic material provided in (i), the molar ratio B$_2$O$_3$:SiO$_2$ is at most 0.02:1, preferably at most 0.01:1, more preferably in the range of from 0.0005:1 to 0.01:1, more preferably from 0.0009:1 to 0.003:1.

12. The process of any of one of embodiments 1 to 11, wherein at least 95 weight-%, preferably at least 98 weight-%, more preferably at least 99 weight-% of the framework of the zeolitic material provided in (i) consist of B, Si, O, and H.

13. The process of any one of embodiments 1 to 12, wherein the tin-ion source according to (ii) is one or more of tin(II) alkoxides, tin(IV) alkoxides, tin(II) salts of organic acids, tin(IV) salts of organic acids, preferably one or more of tin(II) alkoxides having from 1 to 4 carbon atoms, tin(IV) alkoxides having from 1 to 4 carbon atoms, tin(II) salts of organic acids having from 1 to 6 carbon atoms, tin(IV) salts of organic acids having from 1 to 6 carbon atoms.

14. The process of any one of embodiments 1 to 13, wherein the tin-ion source according to (ii) comprises, preferably consists of, tin(II) acetate.

15. The process of any one of embodiments 1 to 14, wherein the acid comprised in the liquid aqueous mixture provided in (ii) is one or more organic acids, or one or more inorganic acids, or one or more organic acids and one or more inorganic acids.

16. The process of embodiment 15, wherein the one or more organic acids are one or more of acetic acid, oxalic acid, and citric acid.

17. The process of embodiment 16, wherein the one or more inorganic acids are one or more of phosphoric acid, sulphuric acid, hydrochloric acid, nitric acid, and methane sulfonic acid.
18. The process of embodiment 15 or 16, wherein the acid comprised in the liquid aqueous mixture provided in (ii) comprises, preferably consists of, acetic acid.
19. The process of embodiment 18, wherein the liquid aqueous mixture comprises the acetic acid in an amount in the range of from 2 to 43 weight-%, preferably in the range of from 10 to 40 weight-%, more preferably in the range of from 15 to 35 weight-%, based on the amount of the liquid aqueous mixture.
20. The process of any one of embodiments 1 to 19, wherein the liquid aqueous mixture provided in (ii) has a pH in the range of from 1 to 5, preferably in the range of from 1 to 3, more preferably in the range of from 1 to 2, as determined via a pH sensitive glass electrode.
21. The process of any one of embodiments 1 to 20, wherein the liquid aqueous mixture provided in (ii) comprises the tin-ion source, calculated as elemental Sn, in an amount in the range of from 1 to 25 weight-%, preferably in the range of from 1.2 to 22 weight-%, more preferably in the range of from 1.5 to 19 weight-%, based on the amount of water comprised in the acidic liquid aqueous mixture.
22. The process of any one of embodiments 1 to 21, wherein at least 95 weight-%, preferably at least 98 weight-%, more preferably at least 99 weight-% of the acidic liquid aqueous mixture provided in (ii) consist of the tin-ion source, the acid, and water.
23. The process of any one of embodiments 1 to 22, wherein preparing the mixture according to (iii) comprises agitating the mixture, preferably mechanically agitating the mixture.
24. The process of any one of embodiments 1 to 23, wherein according to (iii), the mixture is prepared at a temperature of the mixture in the range of from 10 to 40° C., preferably in the range of from 15 to 35° C., more preferably in the range of from 20 to 30° C.
25. The process of any one of embodiments 1 to 24, wherein according to (iii), the mixture is prepared at an absolute pressure in the range of from 0.5 to 2 bar, preferably in the range of from 0.8 to 1.2 bar, more preferably in the range of from 0.9 to 1.1 bar.
26. The process of any one of embodiments 1 to 25, wherein according to (iv), the zeolitic material is dried in one or more of nitrogen and an atmosphere comprising oxygen, preferably air or lean air, more preferably air.
27. The process of any one of embodiment 26, wherein according to (iv), the zeolitic material is dried in a first drying period in nitrogen and wherein in a second drying period, the zeolitic material dried in nitrogen is dried in an atmosphere comprising oxygen, preferably air or lean air, more preferably air.
28. The process of embodiment 26 or 27, wherein according to (iv), the zeolitic material is dried at a temperature, preferably of a temperature of the atmosphere according to embodiment 26 or 27, in the range of from 40 to 90° C., preferably in the range of from 50 to 80° C., more preferably in the range of from 60 to 70° C.
29. The process of any one of embodiments 1 to 28, wherein steps (iii) and (iv) constitute an incipient wetness impregnation.
30. The process of any one of embodiment 1 to 29, further comprising
(v) calcining the dried zeolitic material obtained from (iv).
31. The process of embodiment 30, wherein the dried zeolitic material is calcined for a period of time in the range of from 1 to 24 h, preferably in the range of from 2 to 18 h, more preferably in the range of from 3 to 12 h.
32. The process of embodiment 30 or 31, wherein the dried zeolitic material is calcined in an atmosphere comprising nitrogen.
33. The process of embodiment 30, wherein the atmosphere comprising nitrogen is one or more of pure nitrogen, technical nitrogen, lean air, or air.
34. The process of embodiment 32 or 33, wherein in a first calcination period, the dried zeolitic material is calcined in technical nitrogen, and wherein in a second calcination period, the zeolitic material calcined in technical nitrogen is calcined in air.
35. The process of any one of embodiments 32 to 34, wherein the dried zeolitic material is calcined at a temperature of the atmosphere comprising nitrogen in the range of from 350 to 650° C., preferably from 400 to 600° C., more preferably from 450 to 550° C.
36. The process of any one of embodiments 32 to 35, wherein according to (v), the dried zeolitic material is calcined until the total organic carbon (TOC) content of the zeolitic material is at most 0.2 weight-%.
37. The process of any one of embodiments 1 to 36, preferably 32 to 36, wherein the tin-containing zeolitic material having framework type BEA is obtained in the form of a powder.
38. The process of any one of embodiments 1 to 37, further comprising
(vi) shaping the tin-containing zeolitic material having framework type BEA obtained from (iv) or (v), preferably from (v), obtaining moldings.
39. The process of embodiment 38, wherein the shaping according to (vi) comprises subjecting the tin-containing zeolitic material having framework type BEA obtained from (iv) or (v), preferably from (v), to rapid-drying including spray-drying or spray-granulation, preferably to spray-drying, obtaining the moldings in the form of spray-granules.
40. The process of embodiment 39, wherein according to (vi), the rapid-drying, preferably the spray-drying, is carried out using a binder, preferably a silica binder, or precursor of a binder, obtaining the moldings, preferably the spray-granules which comprise the tin-containing zeolitic material having framework type BEA and the binder.
41. The process of any one of embodiments 38 to 40, further comprising
(vii) calcining the moldings, preferably the spray-granules, obtained from (vi);
(viii) optionally subjecting the moldings, preferably the spray-granules, obtained from (vii) to a water-treatment, wherein the water-treatment comprises treating the molding with liquid water in an autoclave under autogenous pressure at a temperature in the range of from 100 to 200° C.;
(ix) optionally drying and/or calcining the water-treated molding, preferably the spray-granules, obtained from (viii).
42. A tin-containing zeolitic material having framework type BEA comprising $B_2O_3$ and $SiO_2$, wherein the framework additionally comprises tin, wherein in the framework structure of the zeolitic material, the molar ratio $B_2O_3$:$SiO_2$ is at most 0.02:1, preferably at most 0.01:1, more preferably in the range of from 0.0005:1 to 0.01:1, more preferably from 0.0009:1 to 0.003:1, wherein at least 95 weight-%, preferably at least 98 weight-%, more preferably at least 99 weight-% of the framework of the zeolitic material consist of Si, B, O, H, and tin, obtainable or obtained by a process according to any one of embodiments 1 to 35.

43. A tin-containing zeolitic material having framework type BEA comprising $B_2O_3$ and $SiO_2$, wherein the framework additionally comprises tin, wherein in the framework structure of the zeolitic material, the molar ratio $B_2O_3$:$SiO_2$ is at most 0.02:1, preferably at most 0.01:1, more preferably in the range of from 0.0005:1 to 0.01:1, more preferably from 0.0009:1 to 0.003:1, wherein at least 95 weight-%, preferably at least 98 weight-%, more preferably at least 99 weight-% of the framework of the zeolitic material consist of Si, B, O, H, and tin, said tin-containing zeolitic material having framework type BEA having a crystallinity, as determined via XRD according to Reference Example 5, in the range of from 55 to 80%, preferably in the range of from 60 to 70%, and having BET specific surface area determined according to DIN 66131 of at least 400 m²/g, preferably in the range of from 400 to 600 m²/g.

44. The tin-containing zeolitic material of embodiment 43, wherein in the UV-VIS spectrum of the tin-containing zeolitic material, as determined according to Reference Example 2, the ratio of the intensity of the maximum absorption peak which is in the range of from 200 to 220 relative to the intensity of the shoulder which is in the range of from 245 to 260 nm to is in the range of from 2.1 to 8.0, preferably in the range of from 2.3 to 7.0, more preferably in the range of from 2.5 to 6.0.

45. The tin-containing zeolitic material of embodiment 42 to 44, having a tin content in the range of from 0.5 to 20 weight-%, preferably in the range of from 2 to 18 weight-%, based on the total weight of the tin-containing zeolitic material.

46. The tin-containing zeolitic material of any one of embodiments 42 to 45, comprised in moldings, said moldings optionally additionally comprising a binder, preferably a silica binder.

47. The tin-containing zeolitic material of embodiment 46, wherein the moldings are spray-granules, preferably obtained from spray-drying.

48. A molding, preferably a spray-granule, comprising a tin-containing zeolitic material having framework type BEA according to any one of embodiments 42 to 45, and optionally a binder, preferably a silica binder.

49. Use of a tin-containing zeolitic material having framework type BEA according to any one of embodiments 42 to 47 as a catalytically active material, preferably as a catalytically active material in oxidation reactions including Baeyer-Villiger-type oxidation reactions, Dakin-type reactions and Oppenauer-type oxidation reactions, reduction reactions including Meerwein-Ponndorf-Verley-type reduction reactions, aldol condensation reactions, retro-aldol reactions including the reaction of glucose to lactic acid, isomerization reactions including the isomerization of glucose to fructose.

50. Use of a molding according to embodiment 48 as a catalyst, preferably as a catalytically active material in oxidation reactions including Baeyer-Villiger-type oxidation reactions, Dakin-type reactions and Oppenauer-type oxidation reactions, reduction reactions including Meerwein-Ponndorf-Verley-type reduction reactions, aldol condensation reactions, retro-aldol reactions including the reaction of glucose to lactic acid, isomerization reactions including the isomerization of glucose to fructose.

51. The use of embodiment 49 or 50 for Baeyer-Villiger-type oxidation reactions.

52. The use of any one of embodiments 49 to 51, wherein the Baeyer-Villiger-type oxidation reaction is a process, preferably a liquid phase process, for preparing a compound of formula (III)

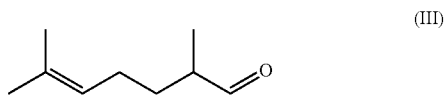

said process comprising
(a) oxidizing a compound of formula (I)

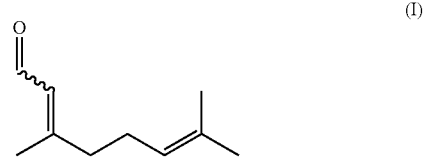

with hydrogen peroxide in the presence of the tin-containing zeolitic material having framework type BEA or in the presence of the molding comprising the tin-containing zeolitic material having framework type BEA, obtaining a reaction mixture comprising a compound of formula (II)

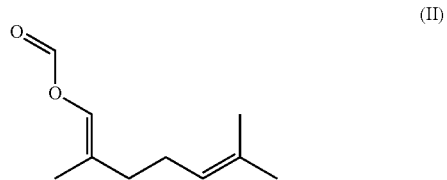

and optionally the compound of formula (III).

53. The use of embodiment 52, wherein in (a), more than 50%, preferably at least 95% of the compound of formula (I) are present as compound of formula (Ia)

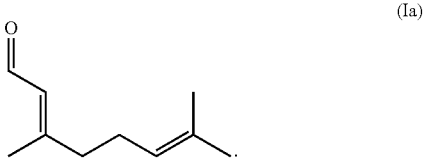

FURTHER ASPECT OF THE INVENTION

According to a further aspect, the present invention also relates to a process for preparing a compound of formula (III)

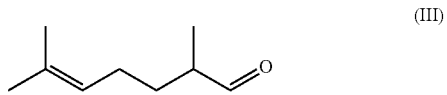

said process comprising (a) oxidizing a compound of formula (I)

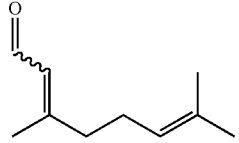
(I)

with hydrogen peroxide in the presence of a Baeyer-Villiger catalyst comprising a tin-containing zeolitic material having framework type BEA according to any one of embodiments 42 to 47 of the first set of embodiments, obtaining a reaction mixture comprising a compound of formula (II)

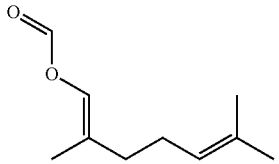
(II)

and optionally the compound of formula (III).

In particular, the tin-containing zeolitic material having framework type BEA is described in the section "The tin-containing zeolitic material as such" hereinabove.

Therefore, the present invention also relates to a process for preparing a compound of formula (III)

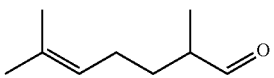
(III)

said process comprising preparing a tin-containing zeolitic material having framework type BEA according to any one of embodiments 1 to 35 of the first set of embodiments hereinabove, and (a) oxidizing a compound of formula (I)

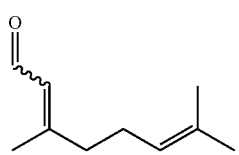
(I)

with hydrogen peroxide in the presence of a Baeyer-Villiger catalyst comprising said tin-containing zeolitic material having framework type BEA, obtaining a reaction mixture comprising a compound of formula (II)

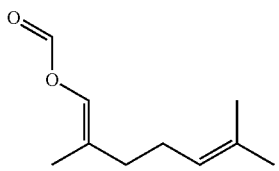
(II)

and optionally the compound of formula (III).

Therefore, according to (a), the tin-containing zeolitic material having framework type BEA is a tin-containing zeolitic material having framework type BEA comprising $B_2O_3$ and $SiO_2$, wherein the framework additionally comprises tin, wherein in the framework structure of the zeolitic material, the molar ratio $B_2O_3:SiO_2$ is at most 0.02:1, preferably at most 0.01:1, more preferably in the range of from 0.0005:1 to 0.01:1, more preferably from 0.0009:1 to 0.003:1, wherein at least 95 weight-%, preferably at least 98 weight-%, more preferably at least 99 weight-% of the framework of the zeolitic material consist of Si, B, O, H. For example, said tin-containing zeolitic material having framework type BEA is obtainable or obtained by the process as described hereinabove in any one of the embodiments 1 to 35 according to the first set of embodiments hereinabove.

Preferably, the tin-containing zeolitic material having framework type BEA according to (a) comprises $B_2O_3$ and $SiO_2$, wherein the framework additionally comprises tin, wherein in the framework structure of the zeolitic material, the molar ratio $B_2O_3:SiO_2$ is at most 0.02:1, preferably at most 0.01:1, more preferably in the range of from 0.0005:1 to 0.01:1, more preferably from 0.0009:1 to 0.003:1, wherein at least 95 weight-%, preferably at least 98 weight-%, more preferably at least 99 weight-% of the framework of the zeolitic material consist of Si, B, O, H, and tin, said tin-containing zeolitic material having framework type BEA having a crystallinity, as determined via XRD according to Reference Example 5, in the range of from 55 to 80%, preferably in the range of from 60 to 70%, and having BET specific surface area determined according to DIN 66131 of at least 400 $m^2/g$, preferably in the range of from 400 to 600 $m^2/g$.

The tin-containing zeolitic material having framework type BEA according to (a) is further preferably characterized in a specific UV-VIS spectrum. In particular, the ratio of the intensity of the maximum absorption peak which is in the range of from 200 to 220 relative to the intensity of the shoulder which is in the range of from 245 to 260 nm to is in the range of from 2.1 to 8.0, preferably in the range of from 2.3 to 7.0, more preferably in the range of from 2.5 to 6.0.

Preferably, the tin-containing zeolitic material having framework type BEA according to (a) has a tin content in the range of from 0.5 to 20 weight-%, preferably in the range of from 2 to 18 weight-%, based on the total weight of the tin-containing zeolitic material. Preferred ranges include, for example, from 2 to 6 weight-% or from 4 to 8 weight-% or from 6 to 10 weight-% or from 8 to 12 weight-% or from 10 to 14 weight-% or from 12 to 16 weight-% or from 14 to 18 weight-%.

According to a first embodiment, in (a), from 45 to 55%, preferably from 47 to 53%, more preferably from 49 to 51% of the compound of formula (I) are present as compound of formula (Ia)

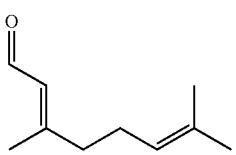

and from 55 to 45%, preferably from 53 to 47% m more preferably from 51 to 49% of the compound of formula (I) are present as compound of formula (Ib)

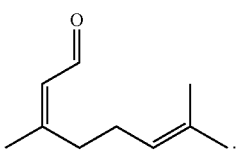

According to a second embodiment, in (a), more than 50%, preferably at least 55%, preferably at least 65%, more preferably at least 75%, more preferably at least 80%, more preferably at least 85%, more preferably from 85 to 90 weight-% of the compound of formula (I) are present as compound of formula (Ia)

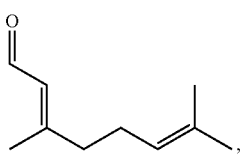

wherein preferably at least 95%, more preferably at least 96%, more preferably at least 97%, more preferably at least 98% of the compound of formula (I) are present as compound of formula (Ia).

According to (a), the compound of formula (I) is oxidized with hydrogen peroxide. Generally, it may be conceivable that a suitable hydrogen peroxide source is employed. Thus, it may conceivable that in the reaction mixture according to (a), the hydrogen peroxide is suitably formed in situ. Preferably, the hydrogen peroxide is employed as an aqueous solution containing hydrogen peroxide. Preferably, the aqueous solution contains the hydrogen peroxide in an amount in the range of from 25 to 85 weight-%, more preferably in the range of from 25 to 80 weight-%, more preferably in the range of from 25 to 75 weight-%, based on the total weight of the aqueous solution. Depending on the solvent which is preferably contained in the reaction mixture, it was found that more than one liquid phase is present when the concentration of the hydrogen peroxide in the aqueous solution is comparatively low, such as in the range of from 25 to 55 weight-% or in the range of from 25 to 45 weight-% or in the range of from 25 to 35 weight-%. Since the presence of more than one liquid phase usually tends to complicate the process design, it is preferred that the aqueous solution contains the hydrogen peroxide in an amount in the range of from 65 to 75 weight-%, based on the total weight of the aqueous solution.

Preferably, at the beginning of the oxidizing in (a), the molar ratio of the compound of formula (I) relative to the hydrogen peroxide is at least 1:1, more preferably in the range of from 10:1 to 1:1, more preferably in the range of from 9:1 to 1:1, more preferably in the range of from 8:1 to 1:1, more preferably in the range of from 7:1 to 1:1, more preferably in the range of from 6:1 to 1:1, more preferably in the range of from 5:1 to 1:1, more preferably in the range of from 4:1 to 1:1, more preferably in the range of from 3:1 to 1:1. More preferably, at the beginning of the oxidizing in (i), the molar ratio of the compound of formula (I) relative to the hydrogen peroxide is in the range of from 2:1 to 1:1, more preferably in the range of from 1.5:1 to 1:1, more preferably in the range of from 1.3:1 to 1:1 such as in the range of from 1.3:1 to 1.2:1 or from 1.2:1 to 1.1:1 or from 1.1:1 to 1:1.

Preferably, the oxidizing in (i) is carried out in solvent. Regarding the chemical nature of the solvent, no specific restrictions exist, provided that the process of the present can be carried out. Preferably, the solvent comprises, more preferably is, an organic solvent. More preferably, the solvent comprises, more preferably is, one or more of alcohols, nitriles, esters, ethers, methyl tert-butyl ether (MTBE), optionally suitably substituted alkanes including halogenated alkanes, preferably chlorinated alkanes including dichloromethane, with methyl tert-butyl ether (MTBE) being preferred.

It may be preferred that the solvent comprises, preferably consists of, one or more alcohols, preferably one or more C4 alcohols, one or more C5 alcohols, one or more C6 alcohols, one or more C7 alcohols, one or more C8 alcohols, one or more C9 alcohols, or a mixture of two or more thereof. Preferably, the one or more alcohols comprise, preferably consist of, one or more of tert-butanol, 2-methyl-2-butanol, n-pentanol, 3-methyl-1-butanol, n-hexanol, 2-methyl-1-pentanol, 3-heptanol, 2-ethyl-1-hexanol, 2-octanol, 1-octanol, 2,4,4-trimethyl-1-hexanol, 2,6-dimethyl-4-heptanol, 2-propyl-1-heptanol, and 2-propyl-5-methyl-1-hexanol. More preferably, the one or more alcohols comprise, preferably consist of, one or more of 2-ethyl-1-hexanol and 3-heptanol.

With regard to the amount of solvent used in (a), no specific restrictions provided that the process of the invention can be carried out. Preferably, at the beginning of the oxidizing in (i), the weight ratio of the compound of formula (I) relative to the solvent is at most 1:2. More preferably, at the beginning of the oxidizing in (a), the weight ratio of the compound of formula (I) relative to the solvent is in the range of from 1:10 to 1:2. Preferred ranges may be from 1:9 to 1:2, more preferably from 1:8 to 1:2, more preferably from 1:7 to 1:2, more preferably from 1:6 to 1:2, more preferably from 1:5 to 1:2, more preferably from 1:4 to 1:2, such as in the range of from 1:4 to 1:3.5 or from 1:3.5 to 1:3 or from 1:3 to 1:2.5 or from 1:2.5 to 1:2.

The temperature at which the oxidizing in (a) is carried out may depend on the solvent used in (a). Preferably, the solvent will be chosen so that the oxidizing in (a) can be carried out at temperature of the reaction mixture in the range of from 30 to 90° C., more preferably in the range of from 35 to 85° C., more preferably in the range of from 40 to 80° C., more preferably in the range of from 45 to 70° C., more preferably in the range of from 50 to 60° C. Therefore, the oxidizing in (a) is preferably carried out at temperature of the reaction mixture in the range of from 30 to 90° C., more preferably in the range of from 35 to 85° C., more preferably in the range of from 40 to 80° C., more preferably in the range of from 45 to 70° C., more preferably in the range of from 50 to 60° C., such as in the range of from 50 to 55° C. or from 55 to 60° C.

It may be preferred that in a first reaction step in (a), the compound of formula (I) and the catalyst, preferably together with the solvent, are heated to the above-mentioned temperature and, once this temperature of the mixture is reached, the hydrogen peroxide, preferably in the form of the aqueous solution, is added to the mixture at this temperature. The oxidizing in (a) can be carried out at more than two reaction temperatures.

According to a preferred embodiment of the present invention, the oxidizing in (a) is carried out in batch mode. Regarding this embodiment, the catalyst used in (a) is preferably employed as powder or as spray-powder or as spray-granulate. During spraying, it is possible that at least one binder and/or with at least one binder precursor is added which is then comprised in the spray-powder or spray-granulate. Suitable binders are described herein under in the context of the moldings which are preferably used in a continuous reaction. It is further preferred that according to this batch mode embodiment, at least 90 weight-%, more preferably at least 91 weight-%, more preferably at least 92 weight-%, more preferably at least 93 weight-%, more preferably at least 94 weight-%, more preferably at least 95 weight-%, more preferably at least 96 weight-%, more preferably at least 97 weight-%, more preferably at least 98 weight-%, more preferably at least 99 weight-% of the catalyst consist of the tin-containing zeolitic material having framework type BEA. Yet further, it may be preferred that according to this embodiment, the oxidizing in (a) is carried out for a period of time in the range of from 3 to 600 min, preferably in the range of from 30 to 500 min, more preferably in the range in the range of from 60 to 400 min. Further, it may be preferred that according to this embodiment, the oxidizing in (a) is carried out for a period of time in the range of from 1 to 25 min, preferably in the range of from 2 to 20 min, more preferably in the range of from 3 to 15 min.

According to a conceivable embodiment of the present invention, the oxidizing in (a) is carried out in continuous mode. According to this embodiment, it is preferred that a molding is employed prepared based on the tin-containing zeolitic material having framework type BEA. In such a process for preparing said molding, the tin-containing zeolitic material having framework type BEA, optionally after further modification, is suitably shaped and optionally post-treated. For the shaping, for example mentioned above in the embodiments in (g), the tin-containing zeolitic material having framework type BEA can be admixed with at least one binder and/or with at least one binder precursor, and optionally with at least one pore-forming agent and/or at least one plasticizing agent. Examples of such binders are metal oxides, such as, for example, $SiO_2$, $Al_2O_3$, $TiO_2$, $ZrO_2$ or MgO or clays or mixtures of two or more of these oxides or mixed oxides of at least two of Si, Al, Ti, Zr, and Mg. Clay minerals and naturally occurring or synthetically produced alumina, such as, for example, alpha-, beta-, gamma-, delta-, eta-, kappa-, chi- or theta-alumina and their inorganic or organometallic precursor compounds, such as, for example, gibbsite, bayerite, boehmite or pseudoboehmite or trialkoxy-aluminates, such as, for example, aluminum triisopropylate, are particularly preferred as $Al_2O_3$ binders. Further conceivable binders might be amphiphilic compounds having a polar and a non-polar moiety and graphite. Further binders might be, for example, clays, such as, for example, montmorillonites, kaolins, metakaoline, hectorite, bentonites, halloysites, dickites, nacrites or anaxites. These binders can be used as such or in the form of suitable precursor compounds which, either during spray-drying or spray-granulation and/or the calcination form the desired binder. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate. In the context of the present invention binders which either completely or partly comprise $SiO_2$, or which are a precursor of $SiO_2$, from which $SiO_2$ is formed, may be preferred. In this context, both colloidal silica and so-called "wet process" silica and so-called "dry process" silica can be used. Particularly preferably this silica is amorphous silica, the size of the silica particles being, for example, in the range of from 5 to 100 nm and the surface area of the silica particles being in the range of from 50 to 500 $m^2/g$. Colloidal silica, preferably as an alkaline and/or ammoniacal solution, more preferably as an ammoniacal solution, is commercially available, inter alia, for example as Ludox®, Syton®, Nalco® or Snowtex®. "Wet process" silica is commercially available, inter alia, for example as HiSil®, Ultrasil®, Vulcasil®, Santocel®, ValronEstersil®, Tokusil® or Nipsil®. "Dry process" silica is commercially available, inter alia, for example as Aerosil®, Reolosil®, Cab-O-Sil®, Fransil® or ArcSilica®. Inter alia, an ammoniacal solution of colloidal silica is preferred in the present invention. Pore forming agents include, but are not limited to, polymers such as polymeric vinyl compounds, such as polyalkylene oxides like polyethylene oxides, polystyrene, polyacrylates, polymethacrylates, polyolefins, polyamides and polyesters, carbohydrates, such as cellulose or cellulose derivatives like methyl cellulose, or sugars or natural fibers. Further suitable pore forming agents may be, for example, pulp or graphite. If desired with regard to the pore characteristics be achieved, a mixture of two or more pore forming agents may be used. In a particularly preferred embodiment, the pore forming agents are removed by calcination. As to the ratio of the amount of the tin-containing zeolitic material having framework type BEA relative to the amount of binder in the molding, it generally can be freely chosen. Generally, the weight ratio of the tin-containing zeolitic material having framework type BEA relative to binder is in the range of from 20:1 to 1:20, preferably from 10:1 to 1:10, more preferably from 1:1 to 1:10. For preparing a molding based on the tin-containing zeolitic material having framework type BEA, at last one pasting agent can be used to provide for an improved processability of the moldable mixture. Conceivable pasting agents are, among others, organic, in particular hydrophilic polymers, such as, for example, carbohydrates like cellulose, cellulose derivatives, such as, for example, methyl cellulose, and starch, such as, for example, potato starch, wallpaper plaster, polyacrylates, polymethacrylates, polyvinyl alcohol, polyvinylpyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propyleneglycol, as pasting agents may be mentioned. Preferably, carbohydrates such as cellulose, cellulose derivatives, water and mixtures of two or more of these compounds, such as water and cellulose or water and cellulose derivatives are used as pasting agent. In a particularly preferred embodiment of the process according to the invention, the at least one pasting agent is removed by drying and/or calcination.

Generally, the process conditions are preferably chosen so that the oxidizing in (a) is carried out so that during oxidizing, the hydrogen peroxide conversion is at least in the range of from 40 to 80%. In particular, during the oxidizing in (a), the temperature of the reaction mixture and the reaction time are preferably chosen so that during oxidizing, the hydrogen peroxide conversion is at least in the range of from 40 to 80%.

From the oxidizing in (a), a reaction mixture is obtained which comprises, as main product of the Baeyer-Villiger oxidation, the compound of formula (II)

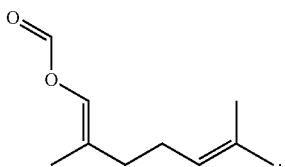

(II)

Additionally, the reaction mixture obtained from (a), may also comprise the compound of formula (III). Since the compound of formula of formula (III)

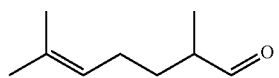

(III)

can be formed from the enol formate of formula (II) by straightforward hydrolysis, the selectivity values to melonal described in the context of the present invention refer to the selectivity values to the sum of the compound of formula (II) and the compound of formula (III) contained in the reaction mixture obtained from (a).

Since melonal is the major product, it is preferred that after (a), the compound of formula (II) is suitably hydrolyzed, obtaining a mixture containing the compound of formula (III). Therefore, the present invention also relates process for preparing a compound of formula (III)

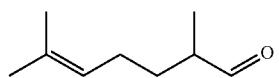

(III)

said process comprising
(a) oxidizing a compound of formula (I)

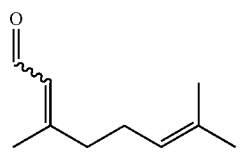

(I)

with hydrogen peroxide in the presence of a catalyst comprising a tin-containing zeolitic material having framework type BEA according to any one of embodiments 42 to 47 of the first set of embodiments, obtaining a reaction mixture comprising a compound of formula (II)

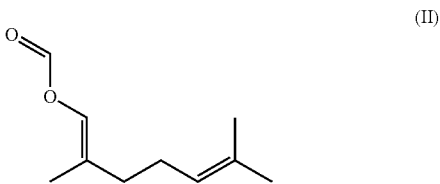

and optionally the compound of formula (III),
wherein after (a), the mixture comprising the compound of formula (II) and optionally the compound of formula (III) is subjected to hydrolyzing conditions, thus hydrolyzing the compound of formula (II), obtaining a mixture containing the compound of formula (III). Preferably, prior to subjecting the mixture comprising the compound of formula (II) and optionally the compound of formula (III) to hydrolyzing conditions, the catalyst comprising a tin-containing zeolitic material having framework type BEA is suitably separated from said mixture. Preferably, prior to subjecting the mixture comprising the compound of formula (II) and optionally the compound of formula (III) to hydrolyzing conditions, more preferably prior to suitably separating the catalyst comprising a tin-containing zeolitic material having framework type BEA from said mixture, the reaction mixture obtained from (a) is cooled, preferably to a temperature in the range of from 5 to 40° C., more preferably in the range of from 8 to 20° C., more preferably in the range of from 10 to 15° C. Preferably, after hydrolyzing the compound of formula (II), the compound of formula (III) is suitably separated from the mixture obtained from said hydrolyzing.

Therefore, the present invention also relates to the process as defined above, further comprising
(b) preferably separating the Baeyer-Villiger catalyst comprising a tin-containing zeolitic material having framework type BEA, from the mixture obtained from (a);
(c) hydrolyzing the compound of formula (II), obtaining a mixture containing the compound of formula (III);
(d) preferably separating the compound of formula (III) from the mixture obtained from (iii).

Regarding the separating according to (b), no specific restrictions exist. If, for example, the process of the invention is carried out in batch mode, it is preferred that the separating comprises, preferably consists of, subjecting the mixture obtained from (a) to filtration. Other separation methods such as phase separation methods are also an option. Generally, it is conceivable that the catalyst contained in the respectively obtained filter cake is re-used, after having been optionally suitably regenerated, as catalyst in (a).

The hydrolyzing in (c) can be carried out by any method which leads to the compound of formula (III). Preferably, for hydrolyzing in (c), an aqueous base is added to the mixture obtained from (a), preferably from (b). Preferably, the aqueous base is an aqueous solution of an inorganic base, more preferably an aqueous solution of a hydroxide, more preferably an aqueous solution of an alkali metal hydroxide, more preferably an aqueous solution of sodium hydroxide. Preferably, the aqueous sodium hydroxide solution contains the sodium hydroxide in an amount in the range of from 1 to 25 weight-%, preferably in the range of from 2 to 20 weight-%, more preferably in the range of from 5 to 15 weight-%, based on the total weight of the aqueous sodium hydroxide solution. Preferably, the aqueous base is added to the reaction mixture at a temperature of the reaction mixture in the range of from 5 to 40° C., preferably in the range of from 8 to 20° C., more preferably in the range of from 10 to 15° C.

By adding the aqueous base to the reaction mixture obtained from the oxidizing in (a) and preferably the separating in (b), an organic phase containing the compound of formula (III) and an aqueous phase are obtained. Therefore, it is preferred that the separating of the compound of formula (III) from the mixture obtained from (c) comprises separating the organic phase from the aqueous phase, wherein the organic phase comprising the compound of formula (III) is preferably suitably washed, preferably with a washing agent comprising water. More preferably, at least 95 weight-%, preferably at least 99 weight-%, more preferably at least 99.9 weight-% of the washing agent consist of water. Said washing is can be carried out at any suitably temperature, wherein the temperature of the washing agent is preferably in the range of from 5 to 40° C., more preferably in the range of from 10 to 30° C., more preferably in the range of from 15 to 25° C.

While it is generally conceivable that the organic phase separated from the aqueous phase and preferably washed is used as such, it is preferred that the compound of formula (III) is suitably separated from the organic phase. Regarding this separating, no specific restrictions exist, provided that the compound of formula (III) is obtained in separated form. Preferably, said separating of the compound of formula (III) from the organic phase comprises distillation, preferably fractional distillation.

Mixtures

Generally, the present invention also relates to a reaction mixture as obtainable or obtained from step (a) of the process of the present invention.

According to the present invention, it was found that the use of the compound of formula (I) wherein more than 50% of the compound of formula (I) are present as compound of formula (Ia) exhibits an advantage over the teaching of the prior art exclusively relating to the use of a 1:1 mixture of the compound of formula (Ia) and of formula (Ib). The starting material of the novel and inventive process is the mixture which is employed as starting mixture for the Baeyer-Villiger oxidation in (a).

Therefore, the present invention also relates to this mixture, in particular to a mixture comprising a compound of formula (I)

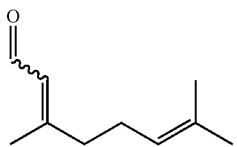
(I)

wherein more than 50%, preferably at least 55%, more preferably at least 60%, more preferably at least 65%, more preferably at least 70%, more preferably at least 75%, more preferably at least 80%, more preferably at least 85%, more preferably at least 90%, more preferably at least 95%, more preferably at least 96%, more preferably at least 97%, more preferably at least 98% of the compound of formula (I) are present as compound of formula (Ia)

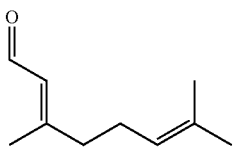
(Ia)

and a Baeyer-Villiger oxidation catalyst which comprises a tin-containing zeolitic material having framework type BEA according to any one of embodiments 42 to 47 of the first set of embodiments. Preferably, this mixture further comprising a solvent, more preferably a solvent as described hereinabove. In said mixture, the weight ratio of the compound of formula (I) relative to the solvent is preferably in the range of from 1:10 to 1:2, preferably in the range of from 1:5 to 1:2, more preferably in the range of from 1:4 to 1:2.

Uses

As mentioned above, it was found that the use of the compound of formula (I) wherein more than 50% of the compound of formula (I) are present as compound of formula (Ia) exhibits an advantage over the teaching of the prior art exclusively relating to the use of a 1:1 mixture of the compound of formula (Ia) and of formula (Ib).

Therefore, the present invention also relates to the use of a compound of formula (I)

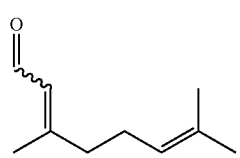
(I)

of which more than 50%, preferably at least 55%, more preferably at least 60%, more preferably at least 65%, more preferably at least 70%, more preferably at least 75%, more preferably at least 80%, more preferably at least 85%, more preferably at least 90%, more preferably at least 95%, more preferably at least 96%, more preferably at least 97%, more preferably at least 98% are present as compound of formula (Ia)

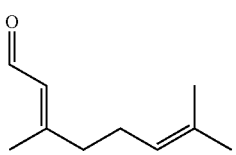
(Ia)

for either increasing the selectivity and/or decreasing the reaction time of the Baeyer-Villiger oxidation of the compound of formula (I) for preparing a compound of formula (III)

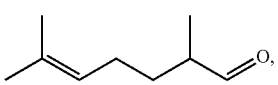
(III)

compared to the respective Baeyer-Villiger oxidation of the compound of formula (I) of which at most 50% are present as compound of formula (Ia), at otherwise identical oxidation conditions, wherein for said Baeyer-Villiger oxidation, a Baeyer-Villiger oxidation catalyst is employed which comprises a tin-containing zeolitic material having framework type BEA according to any one of embodiments 42 to 47 of the first set of embodiments.

Further, the present invention also relates to the use of the starting mixture described above, in particular a mixture comprising a compound of formula (I)

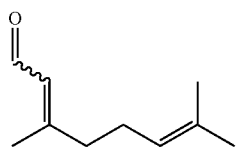
(I)

wherein more than 50%, preferably at least 55%, more preferably at least 60%, more preferably at least 65%, more preferably at least 70%, more preferably at least 75%, more preferably at least 80%, more preferably at least 85%, more preferably at least 90%, more preferably at least 95%, more preferably at least 96%, more preferably at least 97%, more preferably at least 98% of the compound of formula (I) are present as compound of formula (Ia)

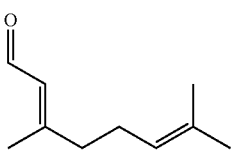
(Ia)

and a Baeyer-Villiger oxidation catalyst which comprises a tin-containing zeolitic material having framework type BEA according to any one of embodiments 42 to 47. Preferably, this mixture further comprising a solvent, more preferably a solvent as described hereinabove. In said mixture, the weight ratio of the compound of formula (I) relative to the solvent is preferably in the range of from 1:10 to 1:2, preferably in the range of from 1:5 to 1:2, more preferably in the range of from 1:4 to 1:2, for either increasing the selectivity and/or decreasing the reaction time of the Baeyer-Villiger oxidation of the compound of formula (I) for preparing a compound of formula (III)

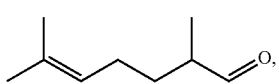
(III)

compared to the respective Baeyer-Villiger oxidation of the compound of formula (I) of which at most 50% are present as compound of formula (Ia), at otherwise identical oxidation conditions, wherein for said Baeyer-Villiger oxidation, a Baeyer-Villiger oxidation catalyst is employed which comprises a tin-containing zeolitic material having framework type BEA according to any one of embodiments 42 to 47 of the first set of embodiments.

Still further, the present invention also relates to the use of said starting mixture for preparing a compound of formula (II)

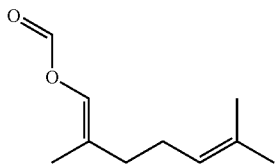
(II)

and/or for preparing a compound of formula (III)

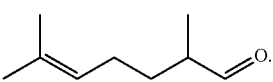
(III)

The further aspect of the present invention is further illustrated by the following second set of embodiments and combinations of embodiments resulting from the given dependencies and back-references.

1. A process for preparing a compound of formula (III)

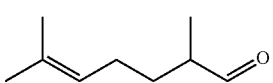
(III)

said process comprising
(a) oxidizing a compound of formula (I)

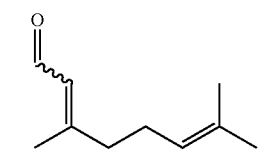
(I)

with hydrogen peroxide in the presence of a Baeyer-Villiger catalyst comprising a tin-containing zeolitic material having framework type BEA according to any one of embodiments 42 to 47 of the first set of embodiments, obtaining a reaction mixture comprising a compound of formula (II)

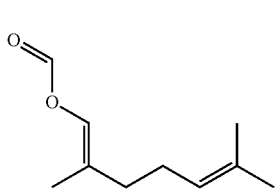
(II)

and optionally the compound of formula (III).

2. The process of embodiment 1, being a liquid-phase process.

3. The process of embodiment 1 or 2, wherein in (a), from 45 to 55%, preferably from 47 to 53%, more preferably from 49 to 51% of the compound of formula (I) are present as compound of formula (Ia)

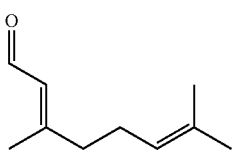
(Ia)

and from 55 to 45%, preferably from 53 to 47% m more preferably from 51 to 49% of the compound of formula (I) are present as compound of formula (Ia)

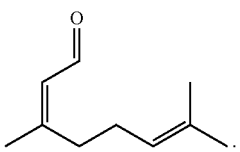
(Ib)

4. The process of embodiment 1 or 2, wherein in (a), more than 50%, preferably at least 55%, preferably at least 65%, more preferably at least 75%, more preferably at least 80%, more preferably at least 85%, more preferably from 85 to 90 weight-% of the compound of formula (I) are present as compound of formula (Ia)

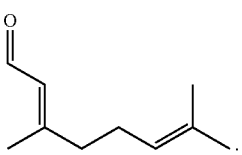
(Ia)

5. The process of embodiment 1 or 2, wherein in (a), at least 95%, preferably at least 96%, more preferably at least 97%, more preferably at least 98% of the compound of formula (I) are present as compound of formula (Ia).
6. The process of any one of embodiments 1 to 5, wherein in (a), the hydrogen peroxide is employed as an aqueous solution containing hydrogen peroxide, wherein the aqueous solution contains the hydrogen peroxide preferably in an amount in the range of from 25 to 85 weight-%, more preferably in the range of from 25 to 80 weight-%, more preferably in the range of from 25 to 75 weight-%, based on the total weight of the aqueous solution.
7. The process of embodiment 6, wherein the aqueous solution contains the hydrogen peroxide in an amount in the range of from 45 to 55 weight-% or in the range of from 65 to 75 weight-%, based on the total weight of the aqueous solution.
8. The process of any one of embodiment 1 to 7, wherein at the beginning of the oxidation in (a), the molar ratio of the compound of formula (I) relative to the hydrogen peroxide is in the range of from 10:1 to 1:1, preferably in the range of from 5:1 to 1:1, more preferably in the range of from 3:1 to 1:1.
9. The process of any one of embodiment 1 to 8, wherein at the beginning of the oxidizing in (a), the molar ratio of the compound of formula (I) relative to the hydrogen peroxide is in the range of from 2:1 to 1:1, preferably in the range of from 1.75:1 to 1:1, more preferably in the range of from 1.5:1 to 1:1.
10. The process of any one of embodiments 1 to 8, wherein the oxidizing in (a) is carried out in a solvent, preferably in an organic solvent, preferably comprising one or more of alcohols, esters, ethers, nitriles, optionally suitably substituted alkanes including halogenated alkanes, preferably chlorinated alkanes including dichloromethane.
11. The process of embodiment 10, wherein the solvent comprises, preferably consists of, one or more alcohols, preferably one or more C4 alcohols, one or more C5 alcohols, one or more C6 alcohols, one or more C7 alcohols, one or more C8 alcohols, one or more C9 alcohols, or a mixture of two or more thereof.
12. The process of embodiment 10 or 11, wherein the one or more alcohols comprise, preferably consist of, one or more of tert-butanol, 2-methyl-2-butanol, n-pentanol, 3-methyl-1-butanol, n-hexanol, 2-methyl-1-pentanol, 3-heptanol, 2-ethyl-1-hexanol, 2-octanol, 1-octanol, 2,4,4-trimethyl-1-hexanol, 2,6-dimethyl-4-heptanol, 2-propyl-1-heptanol, and 2-propyl-5-methyl-1-hexanol.
13. The process of embodiment 11 or 12, wherein the one or more alcohols preferably comprise, more preferably consist of, one or more of 2-ethyl-1-hexanol and 3-heptanol.
14. The process of embodiment 10, wherein the oxidizing in (a) is carried out in one or more ethers, preferably an ether, more preferably methyl tert-butyl ether (MTBE).
15. The process of any one of embodiments 9 to 14, wherein at the beginning of the oxidizing in (a), the weight ratio of the compound of formula (I) relative to the solvent is in the range of from 1:10 to 1:2.
16. The process of any one of embodiments 1 to 15, wherein the oxidizing in (a) is carried out at temperature of the reaction mixture in the range of from 30 to 90° C., preferably in the range of from 40 to 80° C., more preferably in the range of from 50 to 60° C.
17. The process of any one of embodiments 1 to 16, wherein the oxidizing in (a) is carried out in batch mode.
18. The process of any one of embodiments 1 to 17, preferably of embodiment 17, wherein the catalyst is employed as powder or spray-powder.
19. The process of embodiment 18, wherein at least 90 weight-%, preferably at least 95 weight-%, more preferably at least 99 weight-% of the catalyst consist of the tin-containing zeolitic material having framework type BEA.
20. The process of any one of embodiments 1 to 19, preferably of any one of embodiments 17 to 19, wherein the oxidizing in (a) is carried out for a period of time in the range of from 3 to 600 min, preferably in the range of from 30 to 500 min, more preferably in the range in the range of from 60 to 400 min.
21. The process of any one of embodiments 1 to 20, preferably of any one of embodiments 17 to 20, wherein the oxidizing in (a) is carried out for a period of time in the range of from 1 to 25 min, preferably in the range of from 2 to 20 min, more preferably in the range of from 3 to 15 min.
22. The process of any one of embodiments 1 to 16, wherein the oxidizing in (a) is carried out in continuous-mode.
23. The process of embodiment 22, wherein the catalyst is employed as a molding containing the tin-containing zeolitic material having framework type BEA and preferably a binder.
24. The process of embodiment 23, wherein the binder comprises, preferably is, a silica binder.

25. The process of embodiment 23 or 24, wherein the tin-containing zeolitic material having framework type BEA is contained in the molding as powder or spray-powder.
26. The process of any one of embodiments 1 to 25, wherein the oxidizing in (a) is carried out so that during oxidizing, the hydrogen peroxide conversion is at least in the range of from 40 to 80%.
27. The process of any one of embodiments 1 to 26, wherein during the oxidizing in (a), the temperature of the reaction mixture and the reaction time are chosen so that during oxidizing, the hydrogen peroxide conversion is at least in the range of from 40 to 80%.
28. The process of any one of embodiments 1 to 27, further comprising
    (b) preferably separating the Baeyer-Villiger catalyst from the mixture obtained from (a);
    (c) hydrolyzing the compound of formula (II), obtaining a mixture containing the compound of formula (III);
    (d) preferably separating the compound of formula (III) from the mixture obtained from (c).
29. The process of embodiment 28, wherein in (b), the separating comprises, preferably consists of, subjecting the mixture obtained from (a) to filtration.
30. The process of embodiment 29, wherein in (c), the hydrolyzing is carried out by adding an aqueous base to the reaction mixture obtained from the oxidizing in (a) and preferably the separating in (b), obtaining an organic phase containing the compound of formula (III) and an aqueous phase.
31. The process of embodiment 30, wherein the aqueous base comprises, preferably is, an aqueous sodium hydroxide solution.
32. The process of embodiment 31, wherein the aqueous sodium hydroxide solution contains the sodium hydroxide in an amount in the range of from 1 to 25 weight-%, preferably in the range of from 2 to 20 weight-%, more preferably in the range of from 5 to 15 weight-%, based on the total weight of the aqueous sodium hydroxide solution.
33. The process of any one of embodiments 30 to 32, wherein in (iii), the aqueous base is added to the reaction mixture at a temperature of the reaction mixture in the range of from 5 to 40° C., preferably in the range of from 8 to 20° C., more preferably in the range of from 10 to 15° C.
34. The process of any one of embodiments 30 to 33, wherein in (d), the separating of the compound of formula (III) from the mixture obtained from (c) comprises separating the organic phase from the aqueous phase.
35. The process of any one of embodiments 30 to 34, preferably of embodiment 34, wherein the organic phase is washed, preferably with a washing agent comprising water.
36. The process of embodiment 35, wherein at least 95 weight-%, preferably at least 99 weight-%, more preferably at least 99.9 weight-% of the washing agent consist of water.
37. The process of embodiment 35 or 36, wherein the washing is carried out at a temperature of the washing agent in the range of from 5 to 40° C., preferably in the range of from 10 to 30° C., more preferably in the range of from 15 to 25° C.
38. The process of any one of embodiments 30 to 37, preferably of any one of embodiments 34 to 37, more preferably of any one of embodiments 35 to 37, wherein the compound of formula (III) is separated from the organic phase, preferably from the organic phase separated from the aqueous phase, more preferably from the washed organic phase.
39. The process of embodiment 38, wherein the separating of the compound of formula (Ill) from the organic phase comprises distillation, preferably fractional distillation.
40. A mixture, obtainable or obtained by a process according to any one of embodiments 1 to 27.
41. A mixture, obtainable or obtained by a process according to any one of embodiments 28 to 39.
42. A mixture comprising a compound of formula (I)

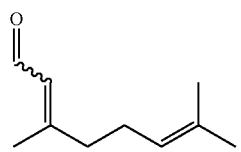

and a Baeyer-Villiger catalyst comprising a tin-containing zeolitic material having framework type BEA according to any one of embodiments 42 to 47 of the first set of embodiments.
43. The mixture of embodiment 42, wherein from 45 to 55%, preferably from 47 to 53%, more preferably from 49 to 51% of the compound of formula (I) are present as compound of formula (Ia)

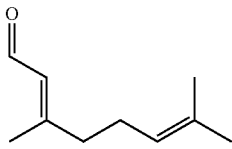

and from 55 to 45%, preferably from 53 to 47% m more preferably from 51 to 49% of the compound of formula (I) are present as compound of formula (Ia)

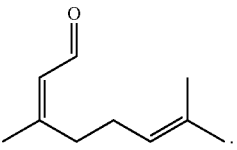

44. The mixture of embodiment 42, wherein more than 50%, preferably at least 55%, preferably at least 65%, more preferably at least 75%, more preferably at least 80%, more preferably at least 85% of the compound of formula (I) are present as compound of formula (Ia)

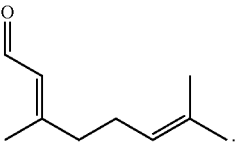

45. The mixture of embodiment 44, wherein from 85 to 90 weight-% of the compound of formula (I) are present as compound of formula (Ia) or wherein at least 95%, preferably at least 96%, more preferably at least 97%, more preferably at least 98% of the compound of formula (I) are present as compound of formula (Ia).
46. The mixture of any one of embodiments 42 to 44, further comprising a solvent wherein the solvent preferably comprises, preferably consists of, methyl tert-butyl ether.
47. The mixture of embodiment 45 or 46, wherein in the mixture, the weight ratio of the compound of formula (I) relative to the solvent is in the range of from 1:10 to 1:2.
48. Use of a mixture according to any one of embodiments 42 to 47 for preparing a compound of formula (II)

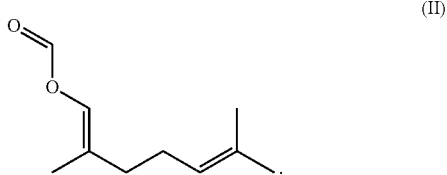

(II)

49. Use of a mixture according to any one of embodiments 42 to 47 for preparing a compound of formula (III)

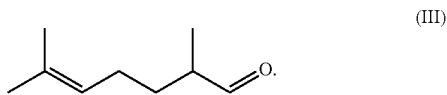

(III)

The present invention is further illustrated by the following reference examples, examples, and comparative examples.

EXAMPLES

Reference Example 1: Preparation of a Deboronated Zeolitic Material Having a BEA Framework Structure 1.1 Preparing a Boron-Containing Zeolitic Material Having a BEA Framework Structure 209 kg de-ionized water were provided in a vessel. Under stirring at 120 rpm (revolutions per minute), 355 kg tetra-ethylammonium hydroxide were added and the suspension was stirred for 10 minutes at room temperature. Thereafter, 61 kg boric acid were suspended in the water and the suspension was stirred for another 30 minutes at room temperature. Subsequently, 555 kg Ludox® AS-40 were added, and the resulting mixture was stirred at 70 rpm for another hour at room temperature. The liquid gel had a pH of 11.8 as determined via measurement with a pH electrode. The finally obtained mixture was transferred to a crystallization vessel and heated to 160° C. within 6 h under a pressure of 7.2 bar and under stirring (140 rpm). Subsequently, the mixture was cooled to room temperature. The mixture was again heated to 160° C. within 6 h and stirred at 140 rpm for additional 55 h. The mixture was cooled to room temperature and subsequently, the mixture was heated for additional 45 h at a temperature of 160° C. under stirring at 140 rpm. 7800 kg de ionized water were added to 380 kg of this suspension. The suspension was stirred at 70 rpm and 100 kg of a 10 weight-% HNO$_3$ aqueous solution was added. From this suspension the boron containing zeolitic material having a BEA framework structure was separated by filtration. The filter cake was then washed with de-ionized water at room temperature until the washing water had a conductivity of less than 150 microSiemens/cm. The thus obtained filter cake was subjected to pre-drying in a nitrogen stream. The thus obtained zeolitic material was subjected, after having prepared an aqueous suspension having a solids content of 15 weight-%, based on the total weight of the suspension, using de-ionized water, to spray-drying in a spray-tower with the following spray-drying conditions:
drying gas, nozzle gas: technical nitrogen
temperature drying gas:
    temperature spray tower (in): 235° C.
    temperature spray tower (out): 140° C.
nozzle:
    top-component nozzle supplier Gerig; size 0
    nozzle gas temperature: room temperature
    nozzle gas pressure: 1 bar
operation mode: nitrogen straight
apparatus used: spray tower with one nozzle
configuration: spray tower-filter-scrubber
gas flow: 1,500 kg/h
filter material: Nomex® needle-felt 20 m$^2$
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material was then subjected to calcination at 500° C. for 5 h. The calcined material had a B$_2$O$_3$:SiO$_2$ molar ratio of 0.045, a total carbon content of (TOC) 0.08 weight-%, a crystallinity determined by XRD of 56%, and a BET specific surface area determined according to DIN 66131 of 498 m$^2$/g. The total pore volume (TPV) determined according to DIN 66134 was 0.4 cm$^3$/g.

1.2 Deboronation—Forming Vacant Tetrahedral Sites 840 kg de-ionized water were provided in a vessel equipped with a reflux condenser. Under stirring at 40 rpm, 28 kg of the spray-dried and calcined zeolitic material described above in 1.1 were employed. Subsequently, the vessel was closed and the reflux condenser put into operation. The stirring rate was increased to 70 rpm. Under stirring at 70 rpm, the content of the vessel was heated to 100° C. within 1 h and kept at this temperature for 20 h. Then, the content of the vessel was cooled to a temperature of less than 50° C. The resulting deboronated zeolitic material having a BEA framework structure was separated from the suspension by filtration under a nitrogen pressure of 2.5 bar and washed four times with deionized water at room temperature. After the filtration, the filter cake was dried in a nitrogen stream for 6 h. The obtained deboronated zeolitic material was subjected, after having re-suspended the zeolitic material in de-ionized water, to spray-drying under the conditions as described in 5.1. The solid content of the aqueous suspension was 15 weight-%, based on the total weight of the suspension. The obtained zeolitic material had a B$_2$O$_3$:SiO$_2$ molar ratio of less than 0.002, a water uptake of 15 weight-%, a crystallinity determined by XRD of 48% and a BET specific surface area determined by DIN 66131 of 489 m²/g.

Reference Example 2: UV-VIS Measurements

The UV-VIS measurements were performed using a PerkinElmer Lambda 950 equipped with a Labsphere 150 mm integrating sphere for the measurement of diffuse reflection (gloss trap closed). The powder cuvette used for the solid samples was filled with the solid samples so that the area measured was completely covered by the sample. As reference, Spectralon standard was used, integration time 0.2 s, scan speed 267 nm/min, spectral range 200-800 nm, measurement at room temperature. The spectra obtained were transformed to Kubelka-Munk spectra.

Reference Example 3: FT-IR Measurements

The FT-IR (Fourier-Transformed-Infrared) measurements were performed on a Nicolet 6700 spectrometer. The powdered material was pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 cm$^{-1}$ at a resolution of 2 cm$^{-1}$. The obtained spectra are represented in a plot having on the x axis the wavenumber (cm$^{-1}$) and on the y axis the absorbance (arbitrary units, a.u.). For the quantitative determination of the peak heights and the ratio between these peaks a baseline correction was carried out. Changes in the 3000-3900 cm$^{-1}$ region were analyzed and for comparing multiple samples, as reference the band at 1880±5 cm$^{-1}$ was taken.

Reference Example 4: Determination of the Water Uptake

Water adsorption/desorption isotherms were performed on a VTI SA instrument from TA Instruments following a step-isotherm program. The experiment consisted of a run or a series of runs performed on a sample material that has been placed on the microbalance pan inside of the instrument. Before the measurement was started, the residual moisture of the sample was removed by heating the sample to 100° C. (heating ramp of 5° C./min) and holding it for 6 h under a nitrogen flow. After the drying program, the temperature in the cell was decreased to 25° C. and kept isothermal during the measurement. The microbalance was calibrated, and the weight of the dried sample was balanced (maximum mass deviation 0.01 weight-%). Water uptake by the sample was measured as the increase in weight over that of the dry sample. First, as adsorption curve was measured by increasing the relative humidity (RH) (expressed as weight-% water in the atmosphere inside of the cell) to which the sample was exposed and measuring the water uptake by the sample as equilibrium. The RH was increased with a step of 10 weight-% from 5% to 85% and at each step the system controlled the RH and monitored the sample weight until reaching the equilibrium conditions after the sample was exposed from 85 weight-% to 5 weight-% with a step of 10% and the change in the weight of the sample (water uptake) was monitored and recorded.

Reference Example 5: Determination of the Crystallinity

The crystallinity was determined according to the method as described in the User Manual DIFFRAC.EVA Version 3, page 105, from Bruker AXS GmbH, Karlsruhe (published February 2003). The respective data were collected on a standard Bruker D8 Advance Diffractometer Series II using a LYNXEYE detector, from 2° to 50° 2theta, using fixed slits, a step size of 0.02° 2theta and a scan speed of 2.4 s/step. The parameters used for estimating the background/amorphous content were Curvature=0 and Threshold=0.8.

Figure 2:
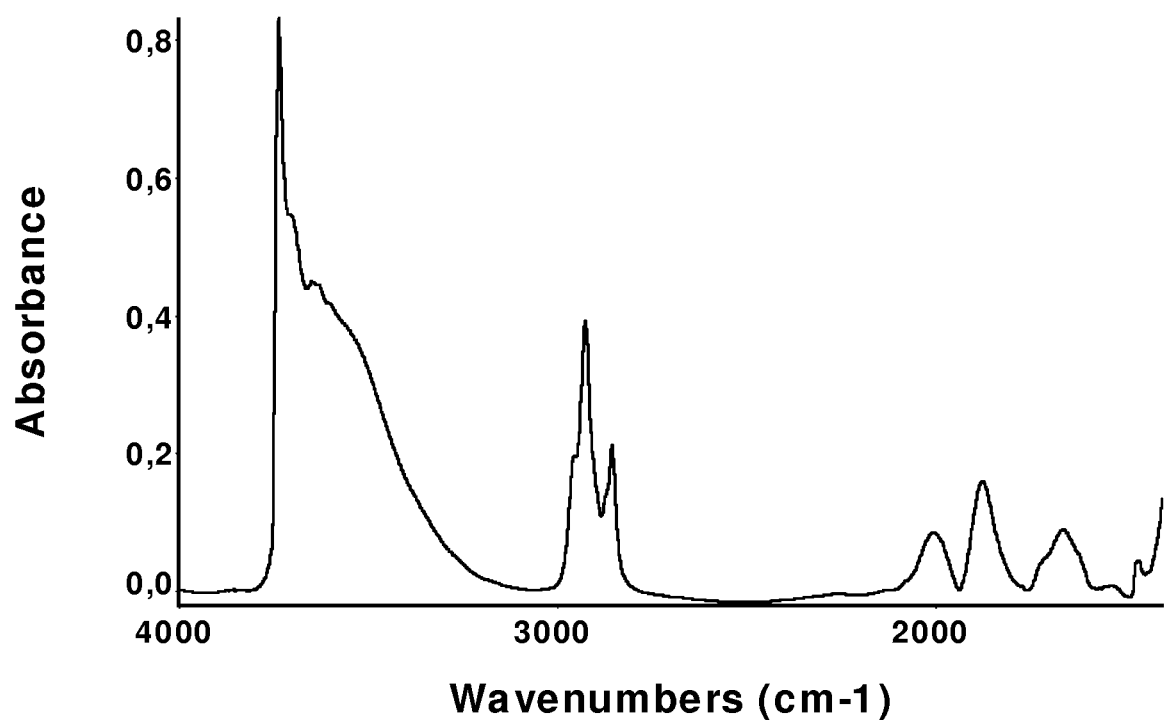

Example 1: Preparation of a Tin-Containing Zeolitic Material Having a BEA Frame-Work Structure Via Impregnation in the Presence of an Acid 3.55 g tin acetate Sn(OAc)$_2$ (from Aldrich) were admixed with 6.25 g acetic acid. 24.75 g de-ionized water were added, resulting in a grey suspension. 25 g of the zeolitic material obtained according to Reference Example 1 were filled in a bowl and admixed with the suspension and thoroughly mixed. The ratio of the volume of the aqueous mixture divided by the mass of the zeolitic material, in cm³/g, to the TPV was 1.28:1. The suspension was dried overnight under air at 60° C. in an oven. In a rotary kiln, the dried suspension was heated with a temperature ramp of 2 K/min to a temperature of 500° C. under nitrogen with a flow rate of 80 Nl/h. Then, the temperature of 500° C. was maintained for 3 h. Subsequently, the nitrogen flow was stopped and replaced by air with a flow rate of 80 Nl/h (Nl/h is defined as flow rate of a gas measured at 101.325 kPa and 0° C. according to DIN 1343). The air flow at 500° C. was maintained for 3 h. Then, the dried and calcined material was cooled to room temperature. 25.1 g tin-containing zeolitic material having a BEA framework structure were obtained. The tin-containing zeolitic material having a BEA framework structure had the following composition: 6.4 weight-% Sn, 40 weight-% Si, <0.1 weight-% C (TOC). The BET surface as determined according to DIN 66133 was 519 m²/g. The crystallinity, as determined according to Reference Example 5, was 68%. The water adsorption, as determined according to Reference Example 4, was 20.4 weight-%. The UV-VIS spectrum, as determined according to Reference Example 2, is shown in FIG. 1. In the UV-VIS spectrum, the ratio of the intensity of the peak of the maximum at about 210 nm relative to the intensity of the shoulder at about 250 nm was 2.6. The FT-IR spectrum, as determined according to Reference Example 3, is shown in FIG. 2.

Figure 3:
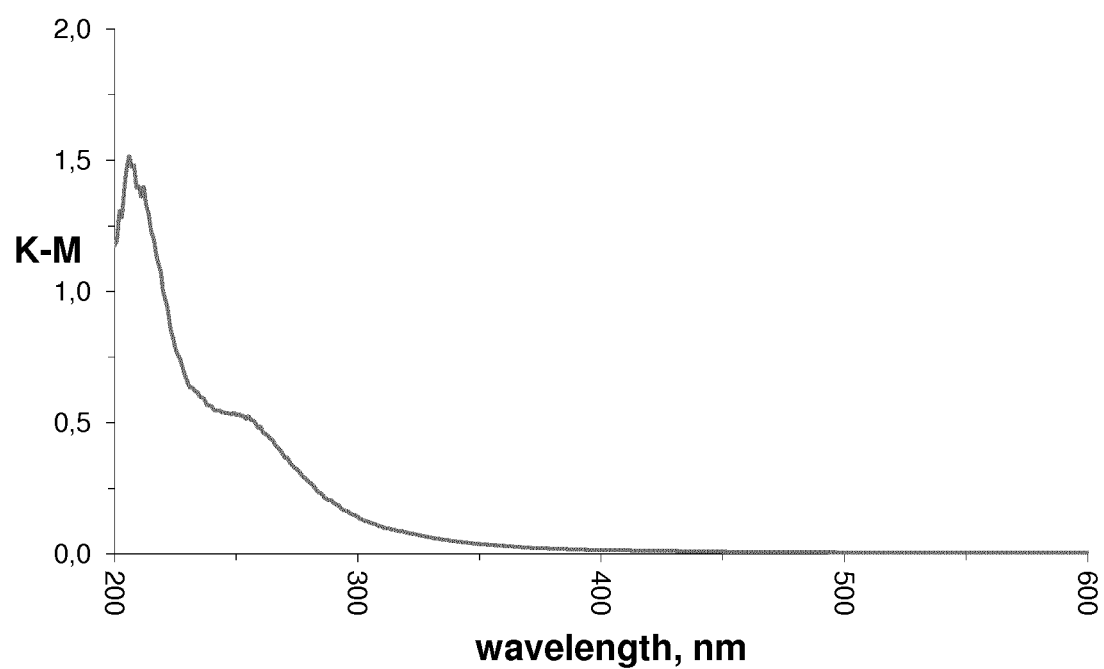
Figure 4:
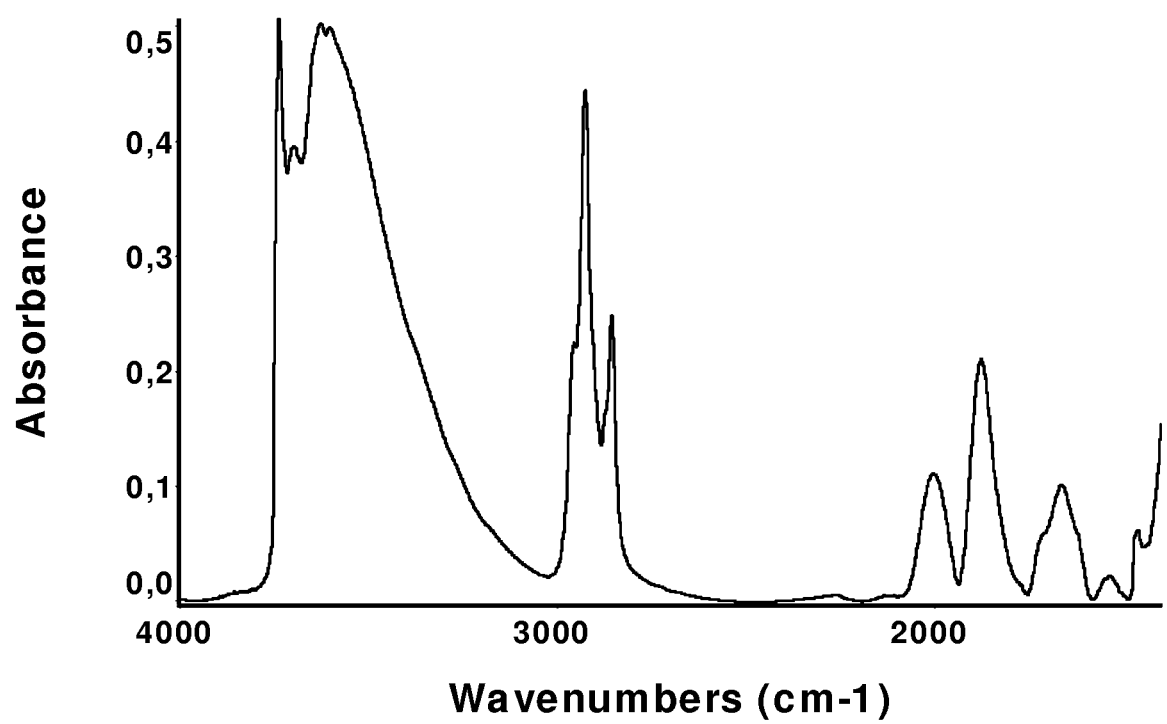

Example 2: Preparation of a Tin-Containing Zeolitic Material Having a BEA Frame-Work Structure Via Impregnation in the Presence of an Acid 14.2 g tin acetate Sn(OAc)$_2$ (from Aldrich) were admixed with 25 g acetic acid. 37.5 g de-ionized water were added, resulting in a grey suspension. 50 g of the zeolitic material obtained according to Reference Example 1 were filled in a bowl and admixed with the suspension and thoroughly mixed. The ratio of the volume of the aqueous mixture divided by the mass of the zeolitic material, in cm³/g, to the TPV was 1.3:1. The suspension was dried overnight under air at 60° C. in an oven. In a rotary kiln, the dried suspension was heated with a temperature ramp of 2 K/min to a temperature of 500° C. under nitrogen with a flow rate of 80 Nl/h. Then, the temperature of 500° C. was maintained for 3 h. Subsequently, the nitrogen flow was stopped and replaced by air with a flow rate of 80 Nl/h. The air flow at 500° C. was maintained for 3 h. Then, the dried and calcined material was cooled to room temperature. 55.1 g tin-containing zeolitic material having a BEA framework structure were obtained. The tin-containing zeolitic material having a BEA framework structure had the following composition: 12.9 weight-% Sn, 38 weight-% Si, <0.1 weight-% C (TOC). The BET surface as determined according to DIN 66131 was 450 m$^2$/g. The crystallinity, as determined according to Reference Example 5, was 63%. The water adsorption, as determined according to Reference Example 4, was 16.9 weight-%. The UV-VIS spectrum, as determined according to Reference Example 2, is shown in FIG. 3. In the UV-VIS spectrum, the ratio of the intensity of the peak of the maximum at about 210 nm relative to the intensity of the shoulder at about 250 nm was 5.9. The FT-IR spectrum, as determined according to Reference Example 3, is shown in FIG. 4.

Figure 9:
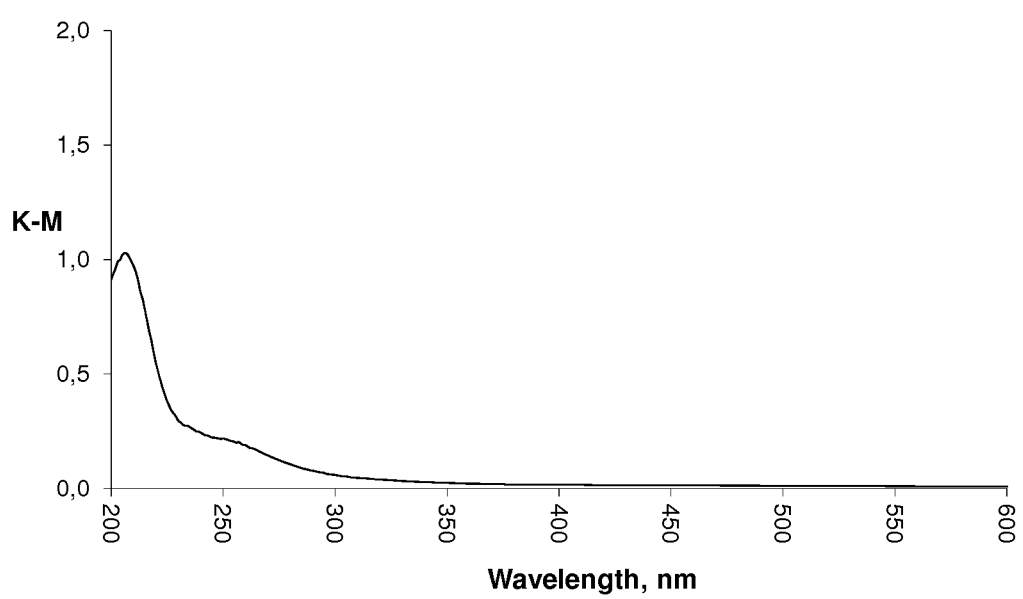

Example 3: Preparation of a Tin-Containing Zeolitic Material Having a BEA Frame-Work Structure Via Impregnation in the Presence of an Acid 7.1 g tin acetate Sn(OAc)$_2$ (from Aldrich) were admixed with 12.5 g acetic acid. 18.75 g de-ionized water were added, resulting in a grey suspension. 25 g of the zeolitic material obtained according to Reference Example 1 were filled in a bowl and admixed with the suspension and thoroughly mixed. The ratio of the volume of the aqueous mixture divided by the mass of the zeolitic material, in cm$^3$/g, to the TPV was 1.36:1. The suspension was dried overnight under air at 60° C. in an oven. In a rotary kiln, the dried suspension was heated with a temperature ramp of 2 K/min to a temperature of 300° C. Then, the temperature of 300° C. was maintained for 3 h under said nitrogen flow. Then, the temperature was raised with a temperature ramp of 2 K/min to a temperature of 500° C. Then, the temperature of 500° C. was maintained for 3 h under said nitrogen flow. Subsequently, the nitrogen flow was stopped and replaced by air with a flow rate of 80 Nl/h. The air flow at 500° C. was maintained for 3 h. Then, the dried and calcined material was cooled to room temperature. 27.4 g tin-containing zeolitic material having a BEA framework structure were obtained. The tin-containing zeolitic material having a BEA framework structure had the following composition: 12.9 weight-% Sn, 38 weight-% Si, <0.1 weight-% C (TOC). The BET surface as determined according to DIN 66131 was 432 m$^2$/g. The crystallinity, as determined according to Reference Example 5, was 63%. The water adsorption, as determined according to Reference Example 4, was 16 weight-%. The UV-VIS spectrum, as determined according to Reference Example 2, is shown in FIG. 9. In the UV-VIS spectrum, the ratio of the intensity of the peak of the maximum at about 210 nm relative to the intensity of the shoulder at about 250 nm was 4.6.

Figure 10:
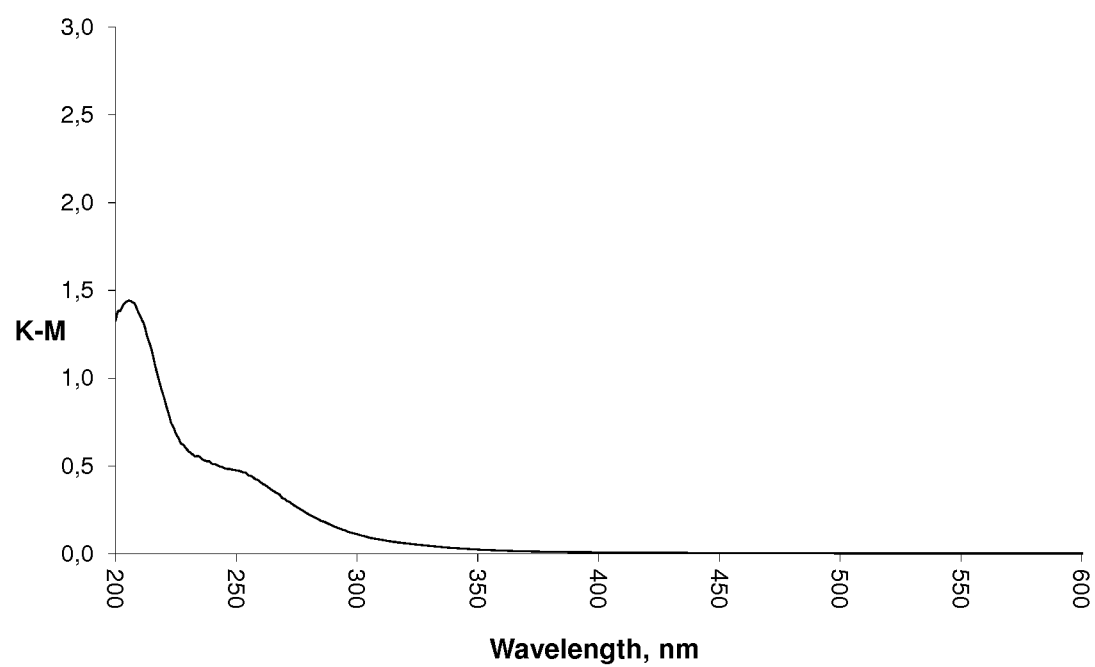
Figure 11:
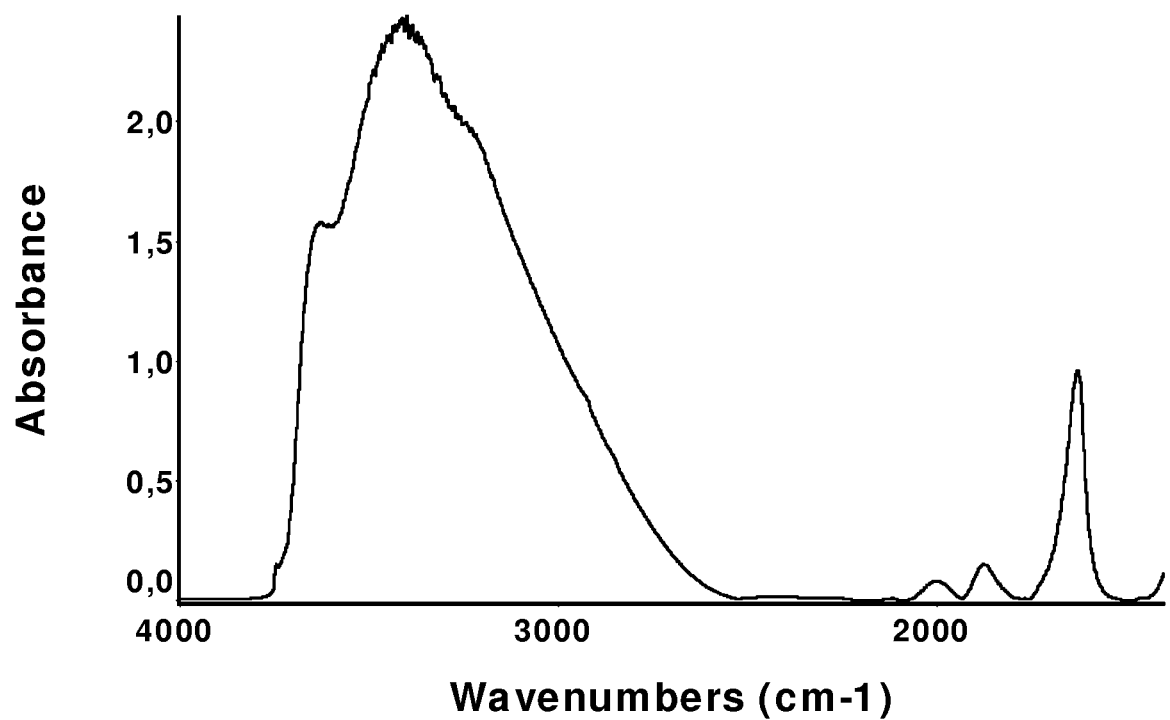

Example 4: Preparation of a Tin-Containing Zeolitic Material Having a BEA Frame-Work Structure Via Impregnation in the Presence of an Acid 7.1 g tin acetate Sn(OAc)$_2$ (from Aldrich) were admixed with 12.5 g acetic acid. 18.75 g de-ionized water were added, resulting in a grey suspension. 25 g of the zeolitic material obtained according to Reference Example 1 were filled in a bowl and admixed with the suspension and thoroughly mixed. The ratio of the volume of the aqueous mixture divided by the mass of the zeolitic material, in cm$^3$/g, to the TPV was 1.36:1. The suspension was dried overnight under air at 60° C. in an oven. In a rotary kiln, the dried suspension was heated with a temperature ramp of 2 K/min to a temperature of 500° C. under N2 80 nL/h. Then, the temperature of 500° C. was maintained for 3 h under said nitrogen flow. Subsequently, the nitrogen flow was stopped and replaced by air with a flow rate of 80 Nl/h. The air flow at 500° C. was maintained for 3 h. Then, the dried and calcined material was cooled to room temperature. 27.2 g tin-containing zeolitic material having a BEA framework structure were obtained. The tin-containing zeolitic material having a BEA framework structure had the following composition: 14.0 weight-% Sn, 37 weight-% Si, <0.1 weight-% C (TOC). The BET surface as determined according to DIN 66131 was 460 m$^2$/g. The crystallinity, as determined according to Reference Example 5, was 68%. The water adsorption, as determined according to Reference Example 4, was 17 weight-%. The UV-VIS spectrum, as determined according to Reference Example 2, is shown in FIG. 10. In the UV-VIS spectrum, the ratio of the intensity of the peak of the maximum at about 210 nm relative to the intensity of the shoulder at about 250 nm was 2.86. The FT-IR spectrum, as determined according to Reference Example 3, is shown in FIG. 11.

Example 5: Preparation of a Tin-Containing Zeolitic Material Having a BEA Frame-Work Structure Via Impregnation in the Presence of an Acid 1.1 Preparing a Boron-Containing Zeolitic Material Having a BEA Framework Structure 259 g de-ionized water were filled in a beaker. Under stirring at 200 r.p.m. (revolutions per minute), 440 g tetraethylammonium hydroxide were added. The stirring was continued for 10 min. Then, 75.6 g boric acid were added and the stirring was continued until a clear solution was obtained (about 30 min). Then, 687.9 g stabilized colloidal silica (Ludox® AS-40) were added and the stirring was continued overnight. The pH of the mixture was 10.8. Then, the mixture was transferred to an autoclave and subjected to hydrothermal crystallization at 160° C. for 48 h under stirring at 140 r.p.m. Then, the mixture was cooled within 5 h to 28° C. After a total of 7 h, it was heated again to 160° C. under stirring at 140 r.p.m. and then stirred at this rate for 96 h at 160° C. After cooling, the mixture was admixed with the double amount of de-ionized water to achieve a pH of the mixture of 8.9. Then, the pH of the mixture was adjusted to a value in the range of from 7-8 with nitric acid (10% in water). Then, the liquid portion of the mixture was removed, and the mixture was washed with de-ionized water until the washing water had a conductivity of less than 150 microSiemens. The resulting boron-containing zeolitic material having a BEA framework structure was dried for 12 h at 120° C. under air and calcined (heating ramp: 2 K/min) for 5 h at 490° C. under air. 285 g boron-containing zeolitic material having a BEA framework structure were obtained, having a B content of 1.5 weight-% and a Si content of 43 weight-%.

1.2 Deboronation and Forming Vacant Tetrahedral Sites

In a stirred vessel, 2,100 g de-ionized water were admixed with 200 g of the boron-containing zeolitic material having a BEA framework structure obtained according to 1.1. The mixture was heated to 100° C. and kept at 100° C. under reflux for 10 h. After cooling and removal of the liquid portion of the mixture (filtration), the solid was washed with de-ionized water. The resulting deboronated zeolitic material having a BEA framework structure was dried (heating ramp: 3 K/min) for 12 h at 120° C. under air and calcined (heating ramp: 2 K/min) for 5 h at 550° C. under nitrogen. 183 g deboronated zeolitic material having a BEA framework structure were obtained, having a B content of 0.1 weight-% and a Si content of 47 weight-%.

Figure 5:
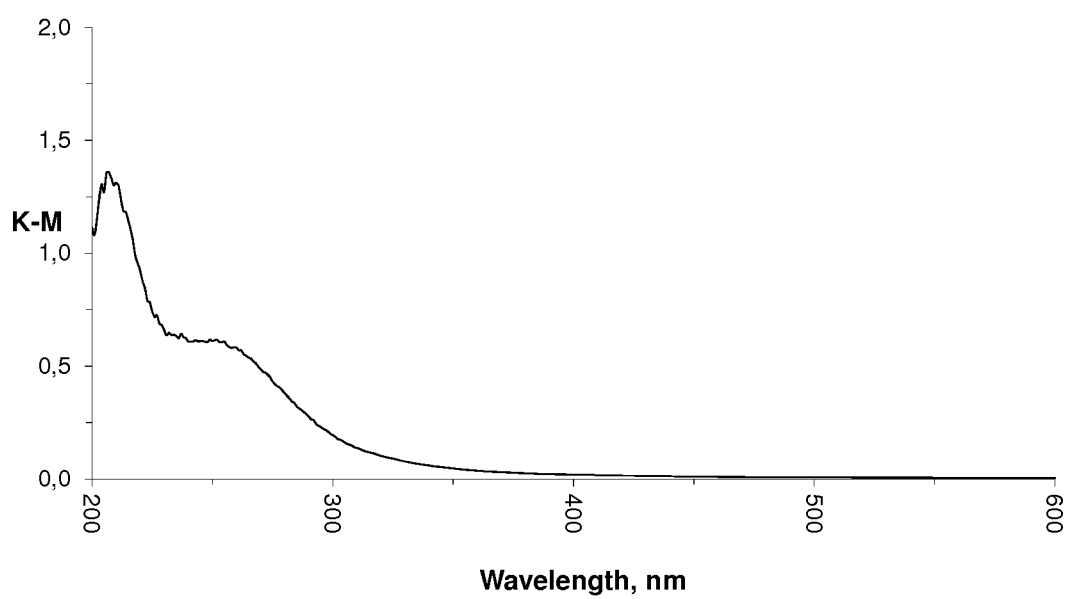
Figure 6:
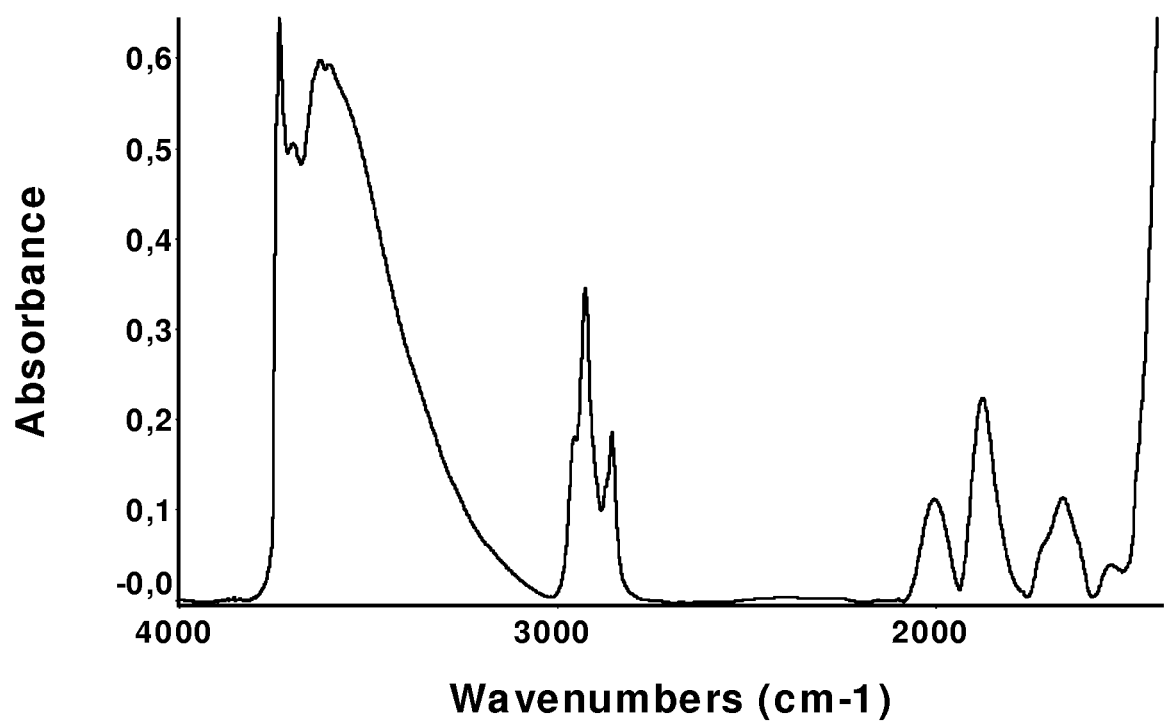

1.3 Incorporating Tin Via Incipient Wetness Impregnation 7.1 g tin acetate Sn(OAc)$_2$ (from Aldrich) were admixed with 12.5 g acetic acid. 18.75 g de-ionized water were added, resulting in a grey suspension. 25 g of the zeolitic material obtained according to Reference Example 1 were filled in a bowl and admixed with the suspension and thoroughly mixed. The ratio of the volume of the aqueous mixture divided by the mass of the zeolitic material, in cm$^3$/g, to the TPV was 1.36:1. The suspension was dried overnight under air at 60° C. in an oven. The suspension was dried overnight under air at 60° C. in an oven. In a rotary kiln, the dried suspension was heated with a temperature ramp of 2 K/min to a temperature of 500° C. under nitrogen with a flow rate of 80 Nl/h. Then, the temperature of 500° C. was maintained for 3 h. Subsequently, the nitrogen flow was stopped and replaced by air with a flow rate of 80 Nl/h. The air flow at 500° C. was maintained for 3 h. Then, the dried and calcined material was cooled to room temperature. 27.2 g tin-containing zeolitic material having a BEA framework structure were obtained. The tin-containing zeolitic material having a BEA framework structure had the following composition: 10.6 weight-% Sn, 37 weight-% Si, <0.1 weight-% C (TOC). The BET surface as determined according to DIN 66131 was 450 m$^2$/g. The crystallinity, as determined according to Reference Example 5, was 60%. The water adsorption, as determined according to Reference Example 4, was 18.9 weight-%. The UV-VIS spectrum, as determined according to Reference Example 2, is shown in FIG. 5. In the UV-VIS spectrum, the ratio of the intensity of the peak of the maximum at about 210 nm relative to the intensity of the shoulder at about 250 nm was 2.2. The FT-IR spectrum, as determined according to Reference Example 3, is shown in FIG. 6.

Figure 7:
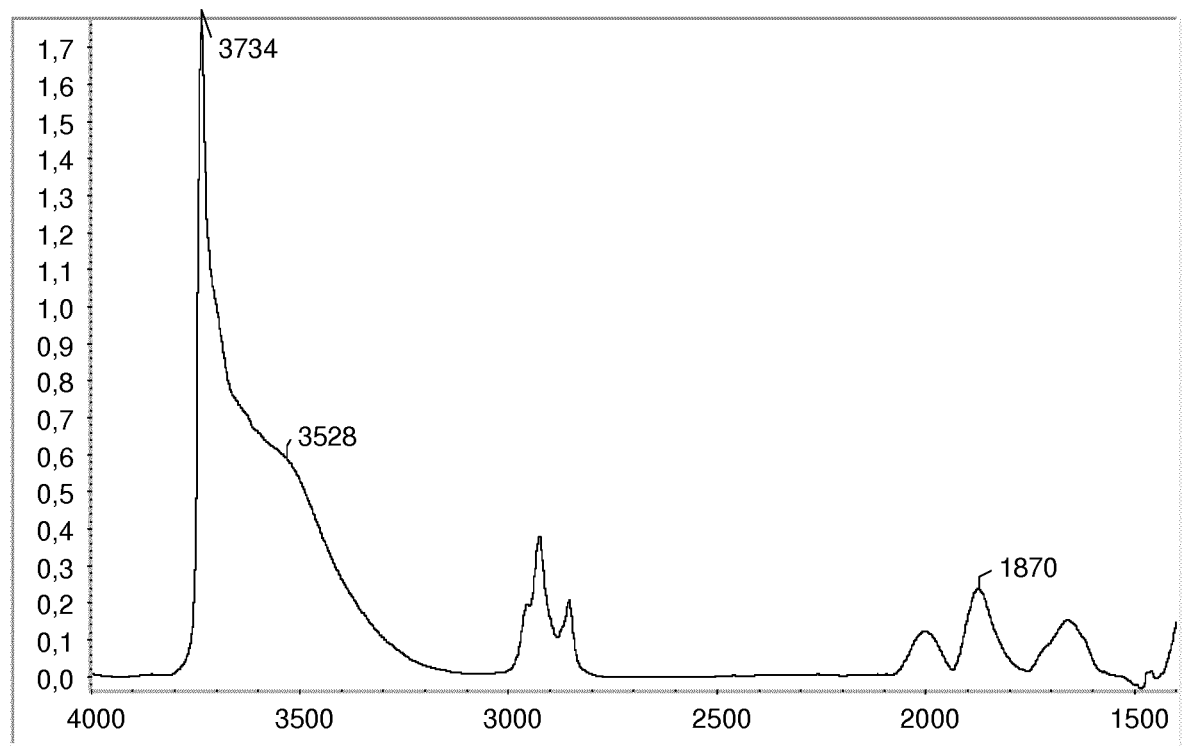

Example 6: Preparation of a Tin-Containing Zeolitic Material Having a BEA Frame-Work Structure Via Impregnation in the Presence of an Acid 1.02 g tin acetate Sn(OAc)$_2$ (from Aldrich) were admixed with 1.80 g acetic acid. 18.75 g de-ionized water were added, resulting in a grey suspension. 25 g of the zeolitic material obtained according to Reference Example 1 were filled in a bowl and admixed with the suspension and thoroughly mixed. The ratio of the volume of the aqueous mixture divided by the mass of the zeolitic material, in cm$^3$/g, to the TPV was 0.88:1. The suspension was dried overnight under air at 60° C. in an oven. In a rotary kiln, the dried suspension was heated with a temperature ramp of 2 K/min to a temperature of 500° C. under nitrogen with a flow rate of 80 Nl/h. Then, the temperature of 500° C. was maintained for 3 h under said nitrogen flow. Subsequently, the nitrogen flow was stopped and replaced by air with a flow rate of 80 Nl/h. The air flow at 500° C. was maintained for 3 h. Then, the dried and calcined material was cooled to room temperature. 23.4 g tin-containing zeolitic material having a BEA framework structure were obtained. The tin-containing zeolitic material having a BEA framework structure had the following composition: 2 weight-% Sn, 42 weight-% Si, <0.1 weight-% C (TOC). The BET surface as determined according to DIN 66131 was 526 m$^2$/g. The crystallinity, as determined according to Reference Example 5, was 70%. The water adsorption, as determined according to Reference Example 4, was 21.9 weight-%. The FT-IR spectrum, as determined according to Reference Example 3, is shown in FIG. 7.

Figure 8:
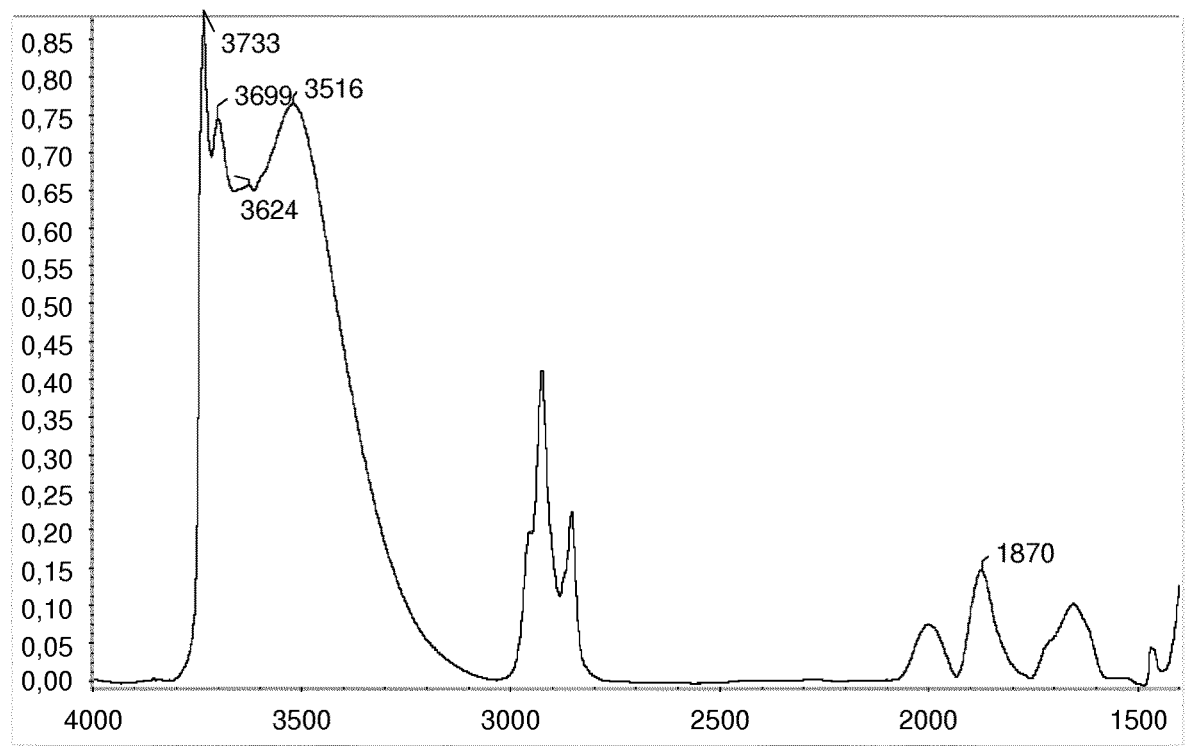

Example 6.1: Post-Treatment of a Tin-Containing Zeolitic Material Having a BEA Framework Structure Having been Prepared Via Impregnation in the Presence of an Acid The tin-containing zeolitic material according to Example 6 having a BEA framework structure was subjected to a post-treatment as follows: 18.46 g de-ionized water were filled in a beaker. Under stirring at 200 r.p.m., 31.36 g tetraethylammonium hydroxide were admixed with the water, followed by stirring for 30 min at 200 r.p.m. Then, 20 g of the tin-containing zeolitic material having a BEA framework structure were admixed with the stirred mixture, and stirring was continued for 1 h. In an oven, the mixture was subjected to a temperature of 160° C. for 36 h. After cooling, the mixture was admixed with the double amount of de-ionized water to achieve a pH of the mixture of 10.9. Then, the pH of the mixture was adjusted to a value in the range of from 7-8 with nitric acid (10% in water). Then, the liquid portion of the mixture was removed, and the mixture was washed with de-ionized water until the washing water had a conductivity of less than 150 microSiemens. The resulting tin-containing zeolitic material having a BEA framework structure was dried for 12 h at 120° C. under air and calcined (heating ramp: 2 K/min) for 5 h at 490° C. under air. 20.2 g tin-containing zeolitic material having a BEA framework structure were obtained. The tin-containing zeolitic material having a BEA framework structure had the following composition: 2 weight-% Sn, 42 weight-% Si, 0.11 weight-% C (TOC). The BET surface as determined according to DIN 66131 was 601 m$^2$/g. The crystallinity, as determined according to Reference Example 5, was 75%. The water adsorption, as determined according to Reference Example 4, was 29.2 weight-%. The FT-IR spectrum, as determined according to Reference Example 3, is shown in FIG. 8.

Comparative Example 1: Preparation of a Tin-Containing Zeolitic Material Having a BEA Framework Structure Via Solid State Ion Exchange 1.1 Preparing a Boron-Containing Zeolitic Material Having a BEA Framework Structure 259 g de-ionized water were provided in a vessel. Under stirring at 120 rpm (rounds per minute), 440 g tetraethylammonium hydroxide were added and the suspension was stirred for 10 minutes at room temperature. Thereafter, 75.6 g boric acid were suspended and the suspension was stirred for another 30 minutes at room temperature. Subsequently, 687.9 g Ludox® AS-40 were added, and the resulting mixture was stirred for another hour at room temperature. The finally obtained mixture was transferred to a crystallization vessel and heated to 160° C. and stirred at 140 rpm for 120 h. The mixture was cooled to room temperature and subsequently. De-ionized water (twice the amount of the mixture), resulting in a mixture having a pH of 10.0. This mixture was adjusted to a pH of 7-8 by adding aqueous HNO$_3$ (10 weight-% HNO$_3$). The mixture was subjected to filtration and the filter cake was washed with de-ionized water until the washing water had a conductivity of less than 150 microSiemens. The thus obtained filter cake was subjected to drying at 120° C. for 2 h under air, followed by calcination at 490° C. for 5 h under air (heating ramp: 2 K/min). The calcined material had a B content of 0.89 weight-%, a Si content of 47 weight-%, a total carbon content of (TOC) of less than 0.1 weight-%, a crystallinity determined by XRD of 42%, and a BET specific surface area determined by DIN 66131 of 257 m$^2$/g.

1.2 Deboronation and Forming Vacant Tetrahedral Sites 2,100 g de-ionized water were passed in a 4 l stirred vessel. Under stirring, 140 g of the material obtained from 1.1 above were added, and the resulting mixture heated to 100° C. The mixture was kept at this temperature under reflux for 10 h. Then, the mixture was cooled to room temperature. The cooled mixture was subjected to filtration and the filter cake was washed with de-ionized water. The thus obtained filter cake was subjected to drying at 120° C. for 12 h under air (heating ramp: 3 K/min), followed by calcination at 550° C. for 5 h under air (heating ramp: 2 K/min). The calcined material had a B content of 0.15 weight-%, a Si content of 49 weight-%, a total carbon content of (TOC) of less than 0.1 weight-%.

Figure 12:
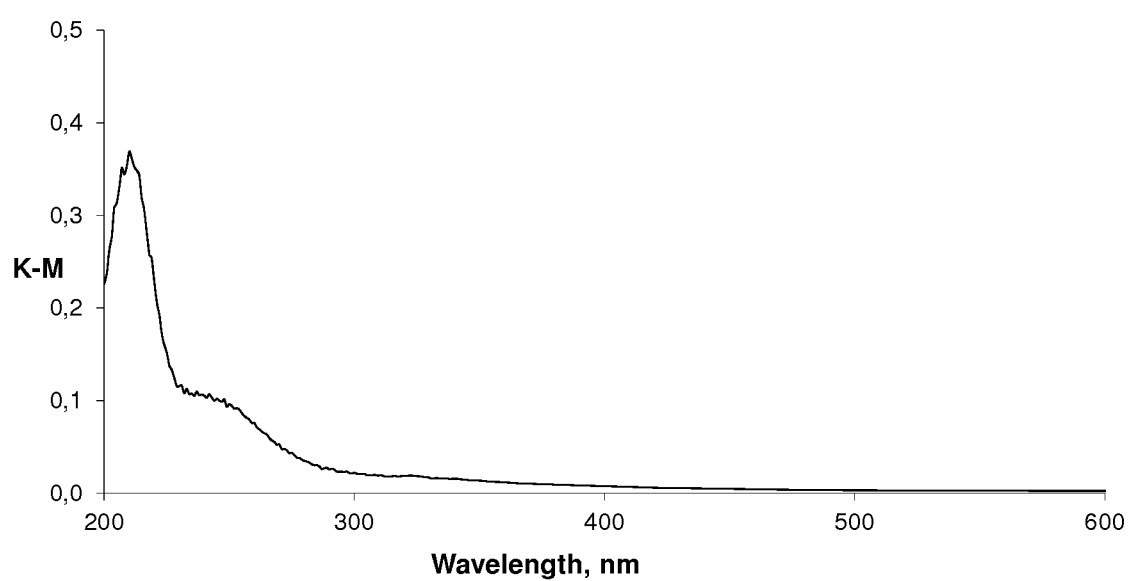

1.3 Incorporating Tin Via Solid-State Ion-Exchange 25 g of the deboronated zeolitic material having a BEA framework structure described in 1.2 above were added to a mixer (mill type Microton MB550) together with 1.02 g of tin(II) acetate (Sn(OAc)$_2$[CAS-Nr:638-39-1]), and the mixture was milled for 15 minutes with 14,000 r.p.m. (rounds per minute). After the milling, the mixture was transferred to a porcelain basket and calcined in air at 500° C. for 3 h under N$_2$ followed by 3 h under air, with a heating ramp of 2 K/min. The obtained powder material had a Sn content of 1.1 weight-%, a silicon (Si) content of 47 weight-%, a B content of less than 0.1 weight-%, and a TOC of less than 0.1 weight-%. The BET specific surface area measured by DIN 66131 was 170 m$^2$/g. The UV-VIS spectrum, as determined according to Reference Example 2, is shown in FIG. 12. In the UV-VIS spectrum, the ratio of the intensity of the peak of the maximum at about 220 nm relative to the intensity of the shoulder at about 250 nm was 4.0.

Figure 13:
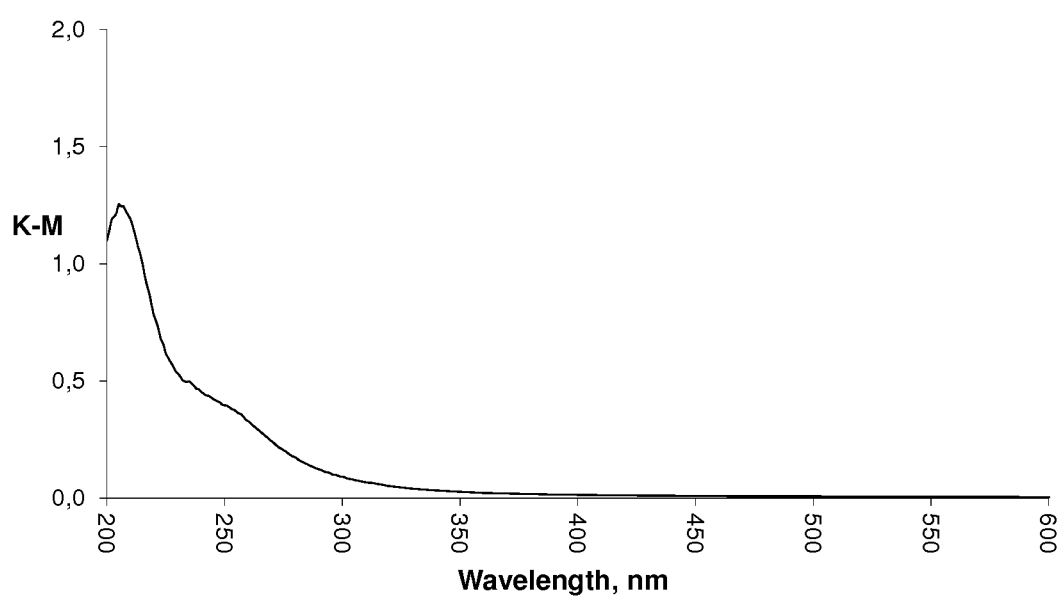

Comparative Example 2: Preparation of a Tin-Containing Zeolitic Material Having a BEA Framework Structure Via Solid State Ion Exchange 30 g of the zeolitic material obtained according to Reference Example 1 were thoroughly admixed for 5 min with 8.52 g tin acetate—which had been milled in ball-milling apparatus for 15 min—, heated in a rotary kiln to 500° C. (temperature ramp: 2 K/min) under nitrogen flow (80 Nl/h) and kept at this temperature under said nitrogen flow for 3 h. Then, the nitrogen flow was switched to air flow (80 Nl/h) and calcination was continued for another 3 h at 500° C. The obtained powder material had a Sn content of 11.8 weight-%, a silicon (Si) content of 37 weight-%, and a TOC of less than 0.1 weight-%. The BET specific surface area measured by DIN 66131 was 386 m$^2$/g. The crystallinity, as determined according to Reference Example 5, was 65%. The UV-VIS spectrum, as determined according to Reference Example 2, is shown in FIG. 13. In the UV-VIS spectrum, the ratio of the intensity of the peak of the maximum at about 210 nm relative to the intensity of the shoulder at about 250 nm was 3.2.

Figure 14:
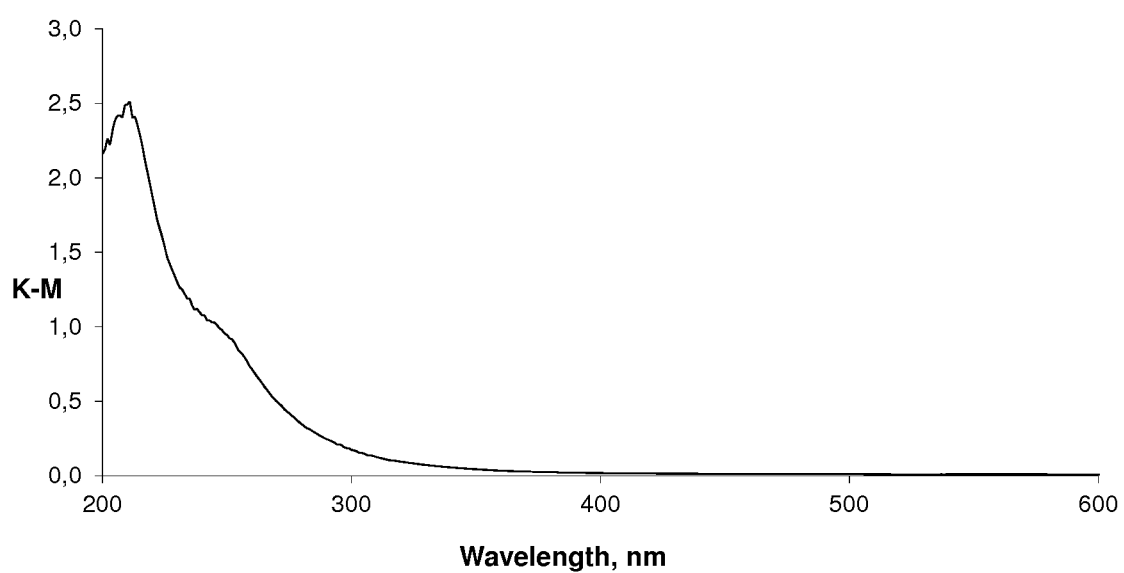

Comparative Example 3: Preparation of a Tin-Containing Zeolitic Material Having a BEA Framework Structure Via Spraying 14.2 g tin acetate were dissolved in 400 ml de-ionized water. Under stirring, 50 g of the zeolitic material obtained according to Reference Example 1 were admixed, and stirring was continued for 3 h at room temperature. The resulting mixture was subjected to spraying using a spray-drying apparatus. The same apparatus and the same spray-drying conditions as described in Reference Example 1 (section 1.1) were used. 50% of the obtained spray-dried material were heated in a rotary kiln to 500° C. (temperature ramp: 2 K/min) under nitrogen flow (80 Nl/h) and kept at this temperature under said nitrogen flow for 3 h. Then, the nitrogen flow was switched to air flow (80 Nl/h) and calcination was continued for another 3 h at 500° C. 8.4 g of tin-containing zeolitic material having a BEA framework structure were obtained. The obtained powder material had a Sn content of 13.4 weight-%, a silicon (Si) content of 38.5 weight-%, and a TOC of less than 0.1 weight-%. The BET specific surface area measured by DIN 66131 was 389 m$^2$/g. The crystallinity, as determined according to Reference Example 5, was 34%. The UV-VIS spectrum, as determined according to Reference Example 2, is shown in FIG. 14. In the UV-VIS spectrum, the ratio of the intensity of the peak of the maximum at about 210 nm relative to the intensity of the shoulder at about 250 nm was 2.5.

Example 7: Baeyer-Villiger Oxidation of Citral (Compound of Formula (I)) with Hydrogen Peroxide in MTBE as Solvent Using a Tin-Containing Zeolitic Material Having a BEA Framework Structure A 1 L glass flask was charged with citral (122.5 g, 98% trans-citral, 2% cis-citral) as indicated in Table 1 below, the zeolitic material according to the Examples and the Comparative Examples above (8.8 g) and MTBE (methyl tert-butyl ether) as solvent (367.5 g) and heated to 50° C. An aqueous solution of hydrogen peroxide 70 w/w %, 29.75 g) was then added and the reaction mixture was stirred. After cooling to room temperature, the resulting solution was filtered and the filtrate was analyzed by GC using dioxane as internal standard. The results are shown in Table 1 below.

TABLE 1

| Results of Example 7 | | | |
|---|---|---|---|
| Example (E) and Comparative Example (CE)/ # | Reaction Time/ min | Sn content of zeolitic material/ weight-% | Citral Conversion/ % | Selectivity [1] based on citral/% |
| E1 | 150 | 6.4 | 35 | 75 |
| E2 | 150 | 12.9 | 39 | 77 |
| E2 [2] | 150 | 12.9 | 29 | 94 |
| E3 | 150 | 12.9 | 36 | 61 |
| E4 | 150 | 14.0 | 34 | 69 |
| E5 | 150 | 10.6 | 31 | 79 |

TABLE 1-continued

Results of Example 7

| Example (E) and Comparative Example (CE)/ # | Reaction Time/ min | Sn content of zeolitic material/ weight-% | Citral Conversion/ % | Selectivity [1] based on citral/% |
|---|---|---|---|---|
| CE1 | 150 | 1.1 | 11 | 63 |
| CE2 | 150 | 11.8 | 23 | 66 |
| CE3 | 150 | 13.4 | 11 | 38 |

[1] molar amount of melonal (compound of formula III)) + molar amount of enol formate (compound of formula (II)) obtained from the reaction divided by the molar amount of citral (compound of formula (I)) converted in the reaction

[2] 24 g hydrogen peroxide (50 w/w %), 70 g citral (98% trans-citral, 2% cis-citral) in 359 g MTBE, and 5 g zeolitic material were used

Results of Example 7

As shown in Example 7, the zeolitic materials according to the invention, prepared by impregnation in the presence of an acid, are characterized by both a high conversion of citral (well above 30% for all Examples) and a high selectivity (above 60% for all Examples). The Sn content of the inventive materials did not play a decisive role, as exemplified, for example, by a comparison of Example 1 and Example 2 exhibiting very similar conversions and selectivities whereas the Sn content according to Example 2 was about twice the Sn content according to Example 1. Compared to the inventive zeolitic materials, other Sn containing materials, prepared, e.g. via solid state ion exchange (Comparative Examples 1 and 2) or spraying (Comparative Example 3), only the materials according to Comparative Examples 1 and 2 exhibited somewhat tolerable selectivity values whereas, for all comparative materials, only very low citral conversions were observed.

Example 8: Comparison of Tin-Containing Zeolitic Materials Having a BEA Framework Structure In the following Table 2, the tin-containing zeolitic material having a BEA framework structure of the present invention, according to the comparative examples and of the prior art are compared with respect to their crystallinity, their BET specific surface area, and their UV-VIS characteristics:

TABLE 2

Comparison of tin-containing zeolitic materials

| Zeolitic material according to | Sn content/ weight-% | BET specific surface area/ $m^2/g$ | Crystallinity/ % | UV-VIS ratio [1] |
|---|---|---|---|---|
| E1 | 6.4 | 519 | 68 | 2.6 |
| E2 | 12.9 | 450 | 63 | 4.6 |
| E3 | 12.9 | 432 | 63 | 5.9 |
| E4 | 14.0 | 460 | 68 | 2.9 |
| E5 | 10.6 | 450 | 60 | 2.2 |
| E6 | 2.0 | 526 | 70 | n.d. [8] |
| CE1 | 1.1 | 170 | n.d. [8] | 4.0 |
| CE2 | 11.8 | 386 | 65 | 3.2 |
| CE3 | 13.4 | 389 | 34 | 2.5 |
| Prior art [2] | 9.3 | 380 | 53 | n.d. [8] |
| Prior art [3] | 12.7 | 395 | 48 | 1.44 |
| Prior art [4] | 12.6 | 405 | 49 | 1.32 |
| Prior art [5] | 9.6 | 423 | 51 | n.d. [8] |
| Prior art [6] | 12.0 | 391 | 44 | 2.0 |
| Prior art [7] | 13.1 | 442 | 44 | 1.75 |

[1] ratio of the intensity of the maximum peak at about 200-220 nm and the intensity of the shoulder at about 250 nm in the UV-VIS spectrum
[2] Example 1 of WO 2015/067654 A
[3] Example 2 of WO 2015/067654 A
[4] Example 3 of WO 2015/067654 A
[5] Comparative Example 1 of WO 2015/067654 A
[6] Comparative Example 2 of WO 2015/067654 A
[7] Comparative Example 3 of WO 2015/067654 A
[8] not determined

Results of Example 8

As shown in Example 8, the zeolitic materials according to the invention exhibit a higher crystallinity. Since, e.g., in catalytic reactions, it is the crystalline material which is active as catalyst, a higher crystallinity means that more active mass of catalytically active material is present. Further, with the regard to the UV-VIS ratio, it is observed that the zeolitic materials according to the invention exhibit higher values which are an indication that, compared to the other materials, a lower amount of extra-framework tin is comprised in the zeolitic materials according to the invention. This means that the zeolitic materials according to the invention have more active sites than the prior art materials. Yet further, it was observed that the zeolitic materials according to the invention exhibit higher BET specific surface areas than the other materials. This means that a larger surface area is available for catalytic reactions.

SHORT DESCRIPTION OF THE FIGURES

FIG. 1 shows the UV-VIS spectrum of the zeolitic material prepared according to Example 1, determined as described in Reference Example 2. The x axis shows the wavelength in nm, with tick marks, from left to right, at 200; 300; 400; 500; 600. The y axis shows the K-M value, with tick marks, from bottom to top, at 0,0; 0,5; 1,0; 1,5; 2,0.

FIG. 2 shows the FT-IR spectrum of the zeolitic material prepared according to Example 1, determined as described in Reference Example 3. The x axis shows the wavenumbers in $cm^{-1}$, with tick marks, from left to right, at 4000; 3000; 2000. The y axis shows the extinction, with tick marks, from bottom to top, at 0,0; 0,2; 0,4; 0,6; 0,8.

FIG. 3 shows the UV-VIS spectrum of the zeolitic material prepared according to Example 2, determined as described in Reference Example 2. The x axis shows the wavelength in nm, with tick marks, from left to right, at 200; 300; 400; 500; 600. The y axis shows the K-M value, with tick marks, from bottom to top, at 0,0; 0,5; 1,0; 1,5; 2,0.

FIG. 4 shows the FT-IR spectrum of the zeolitic material prepared according to Example 2, determined as described in Reference Example 3. The x axis shows the wavenumbers in $cm^{-1}$, with tick marks, from left to right, at 4000; 3000; 2000. The y axis shows the extinction, with tick marks, from bottom to top, at 0,0; 0,1; 0,2; 0,3; 0,4; 0,5.

FIG. 5 shows the UV-VIS spectrum of the zeolitic material prepared according to Example 5, determined as described in Reference Example 2. The x axis shows the wavelength in nm, with tick marks, from left to right, at 200;

300; 400; 500; 600. The y axis shows the K-M value, with tick marks, from bottom to top, at 0,0; 0,5; 1,0; 1,5; 2,0.

FIG. 6 shows the FT-IR spectrum of the zeolitic material prepared according to Example 5, determined as described in Reference Example 3. The x axis shows the wavenumbers in cm$^{-1}$, with tick marks, from left to right, at 4000; 3000; 2000. The y axis shows the extinction, with tick marks, from bottom to top, at −0,00; 0,10; 0,20; 0,30; 0,40; 0,50; 0,60.

FIG. 7 shows the FT-IR spectrum of the zeolitic material prepared according to Example 6, determined as described in Reference Example 3. The x axis shows the wavenumbers in cm$^{-1}$, with tick marks, from left to right, at 4000; 3500; 3000; 2500; 2000; 1500. The y axis shows the extinction, with tick marks, from bottom to top, at 0,0; 0,1; 0,2; 0,3; 0,4; 0,5; 0,6; 0,7; 0,8; 0,9; 1,0; 1.1; 1,2; 1,3; 1,4; 1,5; 1,6; 1,7.

FIG. 8 shows the FT-IR spectrum of the zeolitic material prepared according to Example 6.1, determined as described in Reference Example 3. The x axis shows the wavenumbers in cm$^{-1}$, with tick marks, from left to right, at 4000; 3500; 3000; 2500; 2000; 1500. The y axis shows the extinction, with tick marks, from bottom to top, at 0,00; 0,05; 0,10; 0,15; 0,20; 0,25; 0,30; 0,35; 0,40; 0,45; 0,50; 0,55; 0,60; 0,65; 0,70; 0,75; 0,80; 0,85.

FIG. 9 shows the UV-VIS spectrum of the zeolitic material prepared according to Example 3, determined as described in Reference Example 2. The x axis shows the wavelength in nm, with tick marks, from left to right, at 200; 300; 400; 500; 600. The y axis shows the K-M value, with tick marks, from bottom to top, at 0,0; 0,5; 1,0; 1,5; 2,0.

FIG. 10 shows the UV-VIS spectrum of the zeolitic material prepared according to Example 4, determined as described in Reference Example 2. The x axis shows the wavelength in nm, with tick marks, from left to right, at 200; 250; 300; 350; 400; 450; 500; 550; 600. They axis shows the K-M value, with tick marks, from bottom to top, at 0,0; 0,5; 1,0; 1,5; 2,0.

FIG. 11 shows the FT-IR spectrum of the zeolitic material prepared according to Example 4, determined as described in Reference Example 3. The x axis shows the wavenumbers in cm$^{-1}$, with tick marks, from left to right, at 4000; 3000; 2000. The y axis shows the extinction, with tick marks, from bottom to top, at 0,0; 0,5; 1,0; 1,5; 2,0.

FIG. 12 shows the UV-VIS spectrum of the zeolitic material prepared according to Comparative Example 1, determined as described in Reference Example 2. The x axis shows the wavelength in nm, with tick marks, from left to right, at 200; 300; 400; 500; 600. The y axis shows the K-M value, with tick marks, from bottom to top, at 0,0; 0,1; 0,2; 0,3; 0,4; 0,5.

FIG. 13 shows the UV-VIS spectrum of the zeolitic material prepared according to Comparative Example 2, determined as described in Reference Example 2. The x axis shows the wavelength in nm, with tick marks, from left to right, at 200; 250; 300; 350; 400; 450; 500; 550; 600. The y axis shows the K-M value, with tick marks, from bottom to top, at 0,0; 0,5; 1,0; 1,5; 2,0.

FIG. 14 shows the UV-VIS spectrum of the zeolitic material prepared according to Comparative Example 3, determined as described in Reference Example 2. The x axis shows the wavelength in nm, with tick marks, from left to right, at 200; 300; 400; 500; 600. The y axis shows the K-M value, with tick marks, from bottom to top, at 0,0; 0,5; 1,0; 1,5; 2,0; 2,5; 3,0.

CITED LITERATURE

Hammond C., et al., Simple and Scalable Preparation of Highly Active Lewis Acidic Sn-beta; Angw. Chem. Int. Ed. 2012 (51), pp. 11736-11739

WO 2015/067654 A

The invention claimed is:

1. A process for preparing a tin-containing zeolitic material having framework type BEA, comprising
    (i) providing a zeolitic material having framework type BEA wherein the framework comprises $B_2O_3$ and $SiO_2$, wherein said framework has vacant tetrahedral framework sites;
    (ii) providing a liquid aqueous mixture comprising a tin-ion source and an acid;
    (iii) preparing a mixture of the zeolitic material provided in (i) and the aqueous mixture provided in (ii) obtaining a tin-containing zeolitic material having framework type BEA, wherein the ratio of the volume of the aqueous mixture divided by the mass of the zeolitic material, in cm$^3$/g, to the TPV is in the range of from 0.1:1 to 1.7:1, wherein the TPV is the total pore volume of the zeolitic material in cm$^3$/g as determined by nitrogen absorption according to DIN 66134;
    (iv) drying the zeolitic material obtained from (iii).

2. The process of claim 1, wherein the ratio of the volume of the aqueous mixture divided by the mass of the zeolitic material, in cm$^3$/g, to the TPV is in the range of from 0.2:1 to 1.6:1.

3. The process of claim 1, wherein according to (i), the zeolitic material having framework type BEA having vacant tetrahedral framework sites is provided by a method comprising
    (i.1) providing a zeolitic material having framework type BEA, wherein the framework of the zeolitic starting material comprises $B_2O_3$ and $SiO_2$ and the molar ratio $B_2O_3$:$SiO_2$ is greater than 0.02:1;
    (i.2) creating vacant tetrahedral framework sites by treating the zeolitic material provided in (i.1) with a liquid solvent system, obtaining a zeolitic material having a molar ratio $B_2O_3$:$SiO_2$ of at most 0.02:1, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof;
    (i.3) at least partially separating the zeolitic material obtained from (i.2) from the liquid solvent system, optionally including drying;
    (i.4) optionally calcining the separated zeolitic material obtained from (i.3),
wherein providing a zeolitic material having framework type BEA according to (i.1) optionally comprises:
    (i.1.1) preparing a mixture comprising at least one BEA template compound, at least one source for $SiO_2$ and at least one source for $B_2O_3$;
    (i.1.2) crystallizing the zeolitic material from the mixture prepared in (i.1.1);
    (i.1.3) isolating and/or washing the crystallized material obtained from (i.1.2);
    (i.1.4) subjecting the zeolitic material obtained from (i.1.3) to a heat-treatment stage,
wherein creating vacant tetrahedral framework sites according to (i.2) optionally comprises treating the zeolitic material provided in (i.1) with a liquid solvent system, thereby obtaining a zeolitic material having a molar ratio $B_2O_3$:$SiO_2$, of at most 0.02:1 in an open system at a temperature in the range of from 95 to 105° C.,
and wherein at least partially separating the zeolitic material according to (i.3) comprises at least partially separating the zeolitic material obtained from (i.2) from the liquid solvent system including drying.

4. The process of claim 1, wherein in the framework of the zeolitic material provided in (i), the molar ratio $B_2O_3:SiO_2$ is at most 0.02:1 and wherein at least 95 weight-%, of the framework of the zeolitic material provided in (i) consist of B, Si, O, and H.

5. The process of claim 1, wherein the tin-ion source according to (ii) is one or more of tin(II) alkoxides, tin(IV) alkoxides, tin(II) salts of organic acids, tin(IV) salts of organic acids.

6. The process of claim 1, wherein the acid comprised in the liquid aqueous mixture provided in (ii) is one or more organic acids, or one or more inorganic acids, or one or more organic acids and one or more inorganic acids.

7. The process of claim 6, wherein the liquid aqueous mixture comprises acetic acid in an amount in the range of from 2 to 43 weight-%, based on the amount of the liquid aqueous mixture, wherein the liquid aqueous mixture provided in (ii) has a pH in the range of from 1 to 5, as determined via a pH sensitive glass electrode, and wherein the liquid aqueous mixture provided in (ii) comprises the tin-ion source, calculated as elemental Sn, in an amount in the range of from 1 to 25 weight-%, based on the amount of water comprised in the acidic liquid aqueous mixture.

8. The process of claim 1, wherein at least 95 weight-%, of the acidic liquid aqueous mixture provided in (ii) consist of the tin-ion source, the acid, and water.

9. The process of claim 1, wherein preparing the mixture according to (iii) comprises agitating the mixture, and wherein the mixture is prepared at a temperature of the mixture in the range of from 10 to 40° C.

10. The process of claim 1, wherein according to (iv), the zeolitic material is dried in one or more of nitrogen and an atmosphere comprising oxygen.

11. The process of claim 1, further comprising (v) calcining the dried zeolitic material obtained from (iv), in an atmosphere comprising nitrogen.

12. The process of claim 1, wherein the ratio of the volume of the aqueous mixture divided by the mass of the zeolitic material, in cm³/g, to the TPV is in the range of from 0.4:1 to 1.5:1.

13. The process of claim 1, wherein the ratio of the volume of the aqueous mixture divided by the mass of the zeolitic material, in cm³/g, to the TPV is in the range of from 0.6:1 to 1.4:1.

14. The process of claim 1, wherein in the framework of the zeolitic material provided in (i), the molar ratio $B_2O_3:SiO_2$ is at most 0.01:1 and wherein at least 98 weight-%, of the framework of the zeolitic material provided in (i) consist of B, Si, O, and H.

15. The process of claim 1, wherein in the framework of the zeolitic material provided in (i), the molar ratio $B_2O_3:SiO_2$ is at most in the range of from 0.0005:1 to 0.01:1, and wherein at least 99 weight-% of the framework of the zeolitic material provided in (i) consist of B, Si, O, and H.

16. The process of claim 1, wherein the tin-ion source according to (ii) is tin(II) acetate.

17. A tin-containing zeolitic material having framework type BEA comprising $B_2O_3$ and $SiO_2$, wherein the framework additionally comprises tin, wherein in the framework structure of the zeolitic material, the molar ratio $B_2O_3:SiO_2$ is at most 0.02:1, wherein at least 95 weight-%, of the framework of the zeolitic material consist of Si, B, O, H, and tin, obtained by the process according to claim 1.

18. A catalytically active material comprising the tin-containing zeolitic material having framework type BEA according to claim 17.

19. A tin-containing zeolitic material having framework type BEA comprising $B_2O_3$ and $SiO_2$, wherein the framework additionally comprises tin, wherein in the framework structure of the zeolitic material, the molar ratio $B_2O_3:SiO_2$ is at most 0.02:1, wherein at least 95 weight-%, of the framework of the zeolitic material consist of Si, B, O, H, and tin, said tin-containing zeolitic material having framework type BEA having a crystallinity, as determined via XRD, in the range of from 55 to 80%, and having BET specific surface area determined according to DIN 66131 of at least 400 m²/g.

20. The tin-containing zeolitic material of claim 19, wherein in the UV-VIS spectrum of the tin-containing zeolitic material, the ratio of the intensity of the maximum absorption peak which is in the range of from 200 to 220 relative to the intensity of the shoulder which is in the range of from 245 to 260 nm to is in the range of from 2.1 to 8.0, the tin-containing zeolitic material having a tin content in the range of from 0.5 to 20 weight-%, based on the total weight of the tin-containing zeolitic material.

* * * * *